United States Patent
Walsh et al.

(10) Patent No.: US 11,612,320 B2
(45) Date of Patent: *Mar. 28, 2023

(54) COGNITIVE BENEFIT MEASURE RELATED TO HEARING-ASSISTANCE DEVICE USE

(71) Applicant: Starkey Laboratories, Inc., Eden Prairie, MN (US)

(72) Inventors: Kyle Walsh, Minneapolis, MN (US); Thomas Scheller, Eden Prairie, MN (US); Christopher L. Howes, Eden Prairie, MN (US); David A. Fabry, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 22 days.

This patent is subject to a terminal disclaimer.

(21) Appl. No.: 17/245,777

(22) Filed: Apr. 30, 2021

(65) Prior Publication Data
US 2021/0315457 A1    Oct. 14, 2021

Related U.S. Application Data

(63) Continuation of application No. 16/884,793, filed on May 27, 2020, now Pat. No. 11,012,793, which is a (Continued)

(51) Int. Cl.
*H04R 25/00* (2006.01)
*A61B 5/00* (2006.01)
(Continued)

(52) U.S. Cl.
CPC ............... *A61B 5/002* (2013.01); *A61B 5/16* (2013.01); *A61B 5/4848* (2013.01);
(Continued)

(58) Field of Classification Search
CPC ...... H04R 25/00; H04R 25/55; H04R 25/558; H04R 2225/49; H04R 2460/01
See application file for complete search history.

(56) References Cited

U.S. PATENT DOCUMENTS 7,308,309 B1    12/2007   Koh
9,700,261 B2    7/2017    Lunner
(Continued)

FOREIGN PATENT DOCUMENTS

EP    3107314 A1    12/2016
EP    3185590 A1    6/2017
(Continued)

OTHER PUBLICATIONS

"Oticon Launches HearingFitness to Help People Improve Hearing Health", retrieved from https://www.oticon.com/inside-oticon/news/news/2018/sept-12-hearingfitness, Sep. 12, 2018, 2 pp.
(Continued)

*Primary Examiner* — Suhan Ni
(74) *Attorney, Agent, or Firm* — Shumaker & Sieffert, P.A.

(57) ABSTRACT

A computing system comprising one or more electronic computing devices receives data from a hearing-assistance device. The computing system determines, based on the data received from the hearing-assistance device, a cognitive benefit measure for a wearer of the hearing-assistance device. The cognitive benefit measure being an indication of a change of a cognitive benefit of the wearer of the hearing-assistance device attributable to use of the hearing-assistance device by the wearer of the hearing-assistance device. The computing device outputs an indication of the cognitive benefit measure.

16 Claims, 10 Drawing Sheets

Related U.S. Application Data continuation of application No. 16/110,996, filed on Aug. 23, 2018, now Pat. No. 10,674,285.

(60) Provisional application No. 62/550,353, filed on Aug. 25, 2017.

(51) Int. Cl.
| | | |
|---|---|---|
| *A61B 5/16* | (2006.01) | |
| *A61B 5/12* | (2006.01) | |
| *A61B 5/0205* | (2006.01) | |
| *A61B 5/024* | (2006.01) | |
| *A61B 5/11* | (2006.01) | |

(52) U.S. Cl.
CPC .......... *A61B 5/6803* (2013.01); *H04R 25/30* (2013.01); *H04R 25/407* (2013.01); *H04R 25/505* (2013.01); *H04R 25/554* (2013.01); *A61B 5/02055* (2013.01); *A61B 5/02438* (2013.01); *A61B 5/1118* (2013.01); *A61B 5/123* (2013.01); *A61B 5/7475* (2013.01); *H04R 25/507* (2013.01); *H04R 2225/39* (2013.01); *H04R 2225/41* (2013.01); *H04R 2225/43* (2013.01); *H04R 2225/55* (2013.01); *H04R 2225/61* (2013.01); *H04R 2430/01* (2013.01); *H04R 2460/03* (2013.01)

(56) References Cited

U.S. PATENT DOCUMENTS

| | | | |
|---|---|---|---|
| 9,967,683 B2 | 5/2018 | Solum | |
| 10,117,032 B2 | 10/2018 | Gordon et al. | |
| 10,674,285 B2 | 6/2020 | Walsh et al. | |
| 11,012,793 B2 | 5/2021 | Walsh et al. | |
| 2010/0196861 A1 | 8/2010 | Lunner | |
| 2013/0343584 A1 | 12/2013 | Bennett et al. | |
| 2014/0098981 A1 | 4/2014 | Lunner et al. | |
| 2014/0369537 A1 | 12/2014 | Pontoppidan et al. | |
| 2015/0099469 A1* | 4/2015 | Goldstein | H04W 4/80 455/41.2 |
| 2015/0347499 A1 | 12/2015 | Keen et al. | |
| 2015/0373477 A1* | 12/2015 | Norris | H04M 1/72457 381/303 |
| 2016/0021302 A1 | 1/2016 | Cho et al. | |
| 2016/0055420 A1 | 2/2016 | Karanam et al. | |
| 2016/0057547 A1 | 2/2016 | Burger et al. | |
| 2016/0066107 A1 | 3/2016 | Recker | |
| 2016/0119726 A1 | 4/2016 | Pontoppidan et al. | |
| 2016/0361020 A1 | 12/2016 | LeBoeuf et al. | |
| 2017/0112671 A1 | 4/2017 | Goldstein | |
| 2017/0113057 A1 | 4/2017 | Goodall et al. | |
| 2017/0116380 A1 | 4/2017 | Wiedeback et al. | |
| 2017/0123824 A1 | 5/2017 | Franck | |
| 2017/0180843 A1 | 6/2017 | Perianu et al. | |
| 2017/0258329 A1 | 9/2017 | Marsh | |
| 2018/0035297 A1 | 2/2018 | Cronin | |
| 2018/0109883 A1 | 4/2018 | Blessing et al. | |
| 2020/0196914 A1 | 6/2020 | Sacha | |
| 2020/0268265 A1 | 8/2020 | Walsh et al. | |
| 2020/0273566 A1 | 8/2020 | Bhowmik et al. | |

FOREIGN PATENT DOCUMENTS

| | | |
|---|---|---|
| EP | 3492002 A1 | 6/2019 |
| WO | 2010/079257 A1 | 7/2010 |
| WO | 2010072245 A1 | 7/2010 |
| WO | 2016078709 A1 | 5/2016 |

OTHER PUBLICATIONS

Amieva et al., "Self-Reported Hearing Loss, Hearing Aids, and Cognitive Decline in Elderly Adults: A 25-Year Study," Journal of the American Geriatrics Society, vol. 63, No. 10, Oct. 2015, pp. 2099-2104.

International Preliminary Report on Patentability from International Application No. PCT/US2018/047986, dated Mar. 5, 2020, 9 pp.

International Search Report and Written Opinion of International Application No. PCT/US2018/047986, dated Oct. 15, 2018, 15 pp.

Li et al., "Hearing Impairment Associated with Depression in US Adults, National Health and Nutrition Examination Survey 2005-2010," JAMA Otolaryngology and Neck Surgery, vol. 140, No. 4, Apr. 2014, pp. 293-302.

Urdaneta, "Signia Introduces Made for iPhone Hearing Aid with High-Definition Binaural Hearing," audiologyonline.com, Mar. 24, 2017, 4 pp.

Prosecution History from U.S. Appl. No. 16/110,996, dated Jul. 25, 2019 through Apr. 10, 2020, 33 pp.

Prosecution History from U.S. Appl. No. 16/884,793, dated Oct. 6, 2020 through Jan. 22, 2021, 20 pp.

"The TruHearing App With New Health Insights Broadens the Value and Perception of Hearing Aids," TruHearing, Jan. 18, 2021, 33 pp.

Ferguson et al., "A Randomized Controlled Trial to Evaluate the Benefits of a Multimedia Educational Program for First-Time Hearing Aid Users", Ear and Hearing, Mar. 2016, pp. 123-136.

* cited by examiner

US 11,612,320 B2

COGNITIVE BENEFIT MEASURE RELATED TO HEARING-ASSISTANCE DEVICE USE

This application is a continuation of U.S. patent application Ser. No. 16/884,793, filed May 27, 2020, which is a continuation of U.S. patent application Ser. No. 16/110,996, issued as U.S. Pat. No. 10,674,285, filed Aug. 23, 2018, which claims the benefit of U.S. Provisional Patent Application 62/550,353, filed Aug. 25, 2017, the entire content of each of which is incorporated by reference.

TECHNICAL FIELD

This disclosure relates to hearing-assistance devices.

BACKGROUND

In many people, hearing loss is a gradual process that occurs over many years. As a result, many people grow accustomed to living with reduced hearing without recognizing the auditory experiences and opportunities they are missing. For example, a person might not realize how much less conversation he or she engages in due to his or her hearing loss. As a result of hearing loss, reduced audibility, and reduced social interaction, patients also experience follow-on effects such as dementia, depression, and generally poorer health.

SUMMARY

This disclosure describes techniques for improvement of hearing-assistance device use. As described herein, a computing system receives data from a hearing-assistance device. Based on the received data, the computing system determines a cognitive benefit measure for a wearer of the hearing-assistance device. The cognitive benefit measure may be an indication of a change of a cognitive benefit of the wearer of the hearing-assistance device attributable to use of the hearing-assistance device by the wearer of the hearing-assistance device. Having knowledge of the cognitive benefit measure may provide the wearer of the hearing-assistance device with a way to quantify the value of use of the hearing-assistance device in a way that may not be possible without the use of data from the hearing-assistance device itself. In some examples, a body fitness measure (e.g., a body score) may also be determined, e.g., based on data from a hearing-assistance device. The body fitness measure for the wearer of the hearing-assistance device may be a measure of physical activity in which the wearer of the hearing-assistance device engages while wearing the hearing-assistance device. In some examples, a wellness measure (e.g., a wellness score) may also be determined. The wellness measure may, for example, be determined based on the body fitness measure and the wellness measure.

In one example, this disclosure describes a method comprising: receiving, by a computing system comprising one or more electronic computing devices, data from a hearing-assistance device; determining, by a computing system, based on the data received from the hearing-assistance device, a cognitive benefit measure for a wearer of the hearing-assistance device, the cognitive benefit measure being an indication of a change of a cognitive benefit of the wearer of the hearing-assistance device attributable to use of the hearing-assistance device by the wearer of the hearing-assistance device; and outputting, by the computing system, an indication of the cognitive benefit measure.

In another example, this disclosure describes a computing system comprising: a radio configured to receive data from a hearing-assistance device; and one or more processors configured to: determine, based on the data received from the hearing-assistance device, a cognitive benefit measure for a wearer of the hearing-assistance device, the cognitive benefit measure being an indication of a change of a cognitive benefit of the wearer of the hearing-assistance device attributable to use of the hearing-assistance device by the wearer of the hearing-assistance device; and output an indication of the cognitive benefit measure.

In another example, this disclosure describes a non-transitory computer-readable storage medium having instructions stored thereon that, when executed, cause a computing system to: receive data from a hearing-assistance device; determine, based on the data received from the hearing-assistance device, a cognitive benefit measure for a wearer of the hearing-assistance device, the cognitive benefit measure being an indication of a change of a cognitive benefit of the wearer of the hearing-assistance device attributable to use of the hearing-assistance device by the wearer of the hearing-assistance device; and output an indication of the cognitive benefit measure.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

In this disclosure, ordinal terms such as "first," "second," "third," and so on, are not necessarily indicators of positions within an order, but rather may be used to distinguish different instances of the same thing. Examples provided in this disclosure may be used together, separately, or in various combinations.

Figure 1:
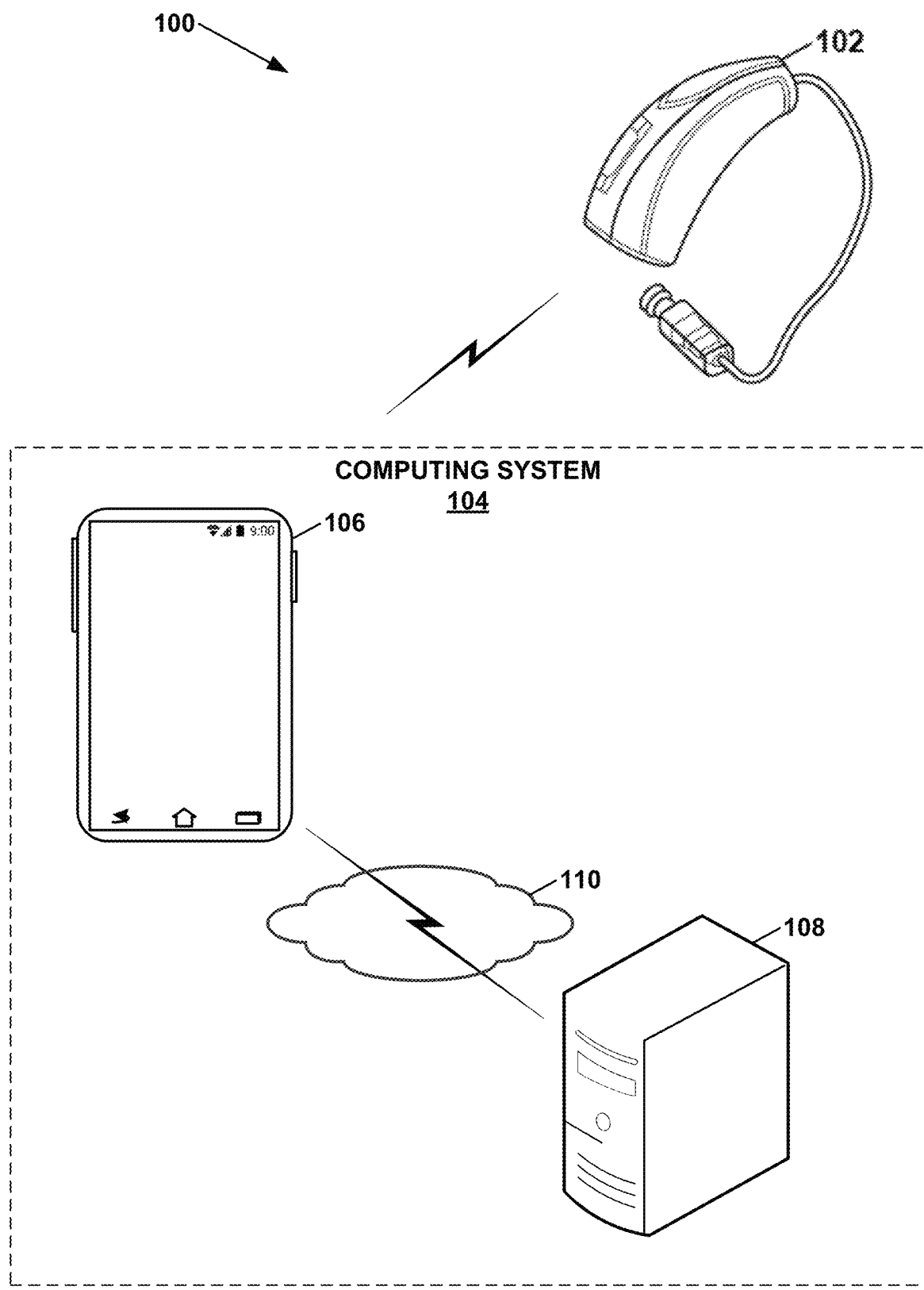
FIG. 1 illustrates an example system for providing cognitive benefit measurements related to use of a hearing-assistance device, in accordance with one or more aspects of this disclosure.

FIG. 1 illustrates an example system 100 for providing cognitive benefit measurements related to use of a hearing-assistance device, in accordance with one or more aspects of this disclosure. In the example of FIG. 1, system 100 comprises a hearing-assistance device 102 and a computing system 104. Computing system 104 comprises one or more electronic devices. For instance, in the example of FIG. 1, computing system 104 comprises a mobile device 106, a server device 108, and a communication network 110.

Hearing-assistance device 102 may comprise one or more of various types of devices configured to provide hearing assistance. For example, hearing-assistance device 102 may comprise a hearing aid device. In another example, hearing-assistance device 102 may comprise a Personal Sound Amplification Product (PSAP). In another example, hearing-assistance device 102 may comprise a hearable with amplification features. In other examples, hearing-assistance device 102 may comprise other types of devices that assist with hearing. The techniques of this disclosure are not limited to the form of hearing-assistance device shown in FIG. 1.

Hearing-assistance device 102 is configured to communicate wirelessly with computing system 104. For example, hearing-assistance device 102 and computing system 104 may communicate wirelessly using a BLUETOOTH™ technology, a WIFI™ technology, or another type of wireless communication technology. In the example of FIG. 1, hearing-assistance device 102 may communicate wirelessly with mobile device 106. In some examples, hearing-assistance device 102 may use a 2.4 GHz frequency band for wireless communication with mobile device 106 or other computing devices.

Mobile device 106 may communicate with server device 108 via communication network 110. Communication network 110 may comprise one or more of various types of communication networks, such as cellular data networks, WIFI™ networks, the Internet, and so on. Mobile device 106 may communicate with server device 108 to store data to and retrieve data from server device 108. Thus, from the perspective of mobile device 106 and hearing-assistance device 102, server device 108 may be considered to be in the "cloud."

Hearing-assistance device 102 may implement a variety of features that help a wearer of hearing-assistance device 102 hear better. For example, hearing-assistance device 102 may amplify the intensity of incoming sound, amplify the intensity of certain frequencies of the incoming sound, or translate or compress frequencies of the incoming sound. In another example, hearing-assistance device 102 may implement a directional processing mode in which hearing-assistance device 102 selectively amplifies sound originating from a particular direction (e.g., to the front of the wearer) while potentially fully or partially canceling sound originating from other directions. In other words, a directional processing mode may selectively attenuate off-axis unwanted sounds. The directional processing mode may help wearers understand conversations occurring in crowds or other noisy environments. In some examples, hearing-assistance device 102 may reduce noise by canceling out or attenuating certain frequencies. Furthermore, in some examples, hearing-assistance device 102 may help a wearer enjoy audio media, such as music or sound components of visual media, by outputting sound based on audio data wirelessly transmitted to hearing-assistance device 102.

As previously mentioned, a person may lose their hearing gradually over the course of many years. Because hearing loss may be a slow process, a person who is gradually losing his or her hearing may grow accustomed to living with impaired hearing and not realize the value added to the person's life by being able to fully access the auditory environment. For instance, the person may not realize how much less time he or she spends in conversation or enjoying audio media because of the person's hearing loss. This may remain true even after a person acquires a hearing-assistance device. That is, because a person having a hearing-assistance device does not always wear the hearing-assistance device, the person may not realize the extent to which the hearing-assistance device enhances his or her life while wearing the hearing-assistance device as opposed to when the person is not wearing the hearing-assistance device.

Research has shown that people who more frequently interact with others and their environments tend to have better cognitive skills and better emotional health, both of which may lead to better health outcomes. However, depression and physical inactivity may be more common among people who seldom converse with others. This problem may be especially acute for older people, who are more likely to have hearing loss.

In accordance with one or more techniques of this disclosure, a cognitive benefit measure is calculated based on data collected by hearing-assistance device 102. In some examples, the cognitive benefit measure is an indication of a change of a cognitive benefit of the wearer of hearing-assistance device 102 attributable to use of hearing-assistance device 102 by the wearer of hearing-assistance device 102. In some examples, hearing-assistance device 102 calculates the cognitive benefit measure. In other examples, the cognitive benefit measure is calculated by one or more computing devices of computing system 104. For instance, in the example of FIG. 1, mobile device 106 or server device 108 may calculate the cognitive benefit measure. For ease of explanation, many of the examples of this disclosure describe computing system 104 calculating the cognitive benefit measure. However, these examples can be adapted to scenarios where hearing-assistance device 102 calculates the cognitive benefit measure.

As described herein, computing system 104 may calculate a cognitive benefit measure for a wearer of hearing-assistance device 102 based on a plurality of sub-components of the cognitive benefit measure. For example, as part of determining the cognitive benefit measure, computing system 104 may determine a plurality of sub-components of the cognitive benefit measure and may determine the cognitive benefit measure based on the plurality of sub-components of the cognitive benefit measure. In some examples, hearing-assistance device 102 determines one or more of the sub-components of the cognitive benefit measure. In some examples, the sub-components include one or more of an "audibility" sub-component, an "intelligibility" sub-component, a "comfort" sub-component, a "focus" sub-component, a "sociability" sub-component, and a "connectivity" sub-component. In some examples, each of the sub-components shares a common range (e.g., from 0 to 100), which may make combination of data efficient. In some examples, computing system 104 may reset each of the sub-components for each scoring period. For instance, computing system 104 may reset the values of the sub-components once per day or other recurrence period.

The audibility sub-component for a wearer of hearing-assistance device 102 is a measure of the improvement in audibility provided to the wearer by hearing-assistance device 102. The audibility sub-component may be considered the amount of environmental sounds that are quieter than the wearer's unaided audiometric thresholds, but that are made audible through amplification by hearing-assistance device 102, scaled to a range used by the other sub-components. In other words, the audibility sub-component is related to hearing more quiet sounds in the wearer's environment. To determine the audibility sub-component, computing system 104 may compare a patient's hearing thresholds to a standardized stimulus response across frequency. For instance, in some examples, the audibility sub-component is calculated by subtracting the percentage of a standardized sound stimulus (e.g., a moderate-level (65 dB SPL) long-term averaged speech input) that is audible without a hearing-assistance device from the percentage of sound that is audible with a hearing-assistance device; both percentages are calculated by dividing the number of audible frequency channels in hearing-assistance device 102 by the number of total channels in the device. A channel in a hearing-assistance device is a subset of frequencies over which the processing of incoming sound can be different from that at other frequencies. For example, a hearing aid channel may have a highpass cutoff of 1480 Hz, and a lowpass cutoff of 1720 Hz. So, the "total channels" in a hearing aid are the number of distinct divisions of frequency. An "audible channel" is one wherein the level of the input stimulus (in dB SPL) plus the gain applied to the stimulus (in dB) results in an overall level that is above the hearing threshold of the listener in that frequency range. Each of the unaided thresholds corresponds to a different frequency. A wearer of hearing-assistance device 102 is unable to hear the frequency corresponding to an unaided threshold if an intensity of a sound at the corresponding frequency is below the unaided threshold. In one example, audibility sub-component is calculated as a number of frequency bands made audible by hearing-assistance device 102 divided by a total number of frequency bands handled by hearing-assistance device 102. In this example, each of the frequency bands may be a contiguous range within a frequency spectrum.

The intelligibility sub-component for the wearer of hearing-assistance device 102 is a numerical estimate of the improvement in speech understanding provided to the wearer by hearing-assistance device 102. The intelligibility sub-component may be considered a measure of understanding more words in conversation. In some examples, the intelligibility sub-component is a percentage improvement in intelligibility. For instance, in one such example, the intelligibility sub-component is equal to a first value multiplied by 100, where the first value is equal to a third value subtracted from a second value. The second value is equal to an aided intelligibility score, and the third value is equal to an unaided intelligibility score. The intelligibility scores both are calculated from the Speech Intelligibility Index (SII), which is a standardized measure of intelligibility. Of course, other measures of intelligibility scaled to the same range as the other sub-components may be used.

The comfort sub-component for the wearer of hearing-assistance device 102 is a numerical value indicating a measure of noise reduction provided by hearing-assistance device 102. The comfort sub-component may be considered a measure of noise reduction in the wearer's environment. In some examples, the comfort sub-component is equal to an average or a sum of noise reduction. For instance, in one such example, the comfort sub-component is equal to a first value. In this example, the first value is equal to a sum of the average noise reduction (in dB) across memories and environments, weighted by the time spent in each memory in a set of one or more memories and each environment in a set of one or more environments, scaled to the standardized range used in the other sub-components. In this example, hearing-assistance device 102 comprises different memories, which have different signal processing schemes tailored to specific listening situations. For example, there is a "Restaurant" memory, a "Music" memory, and so on. Each of the environments is an acoustic situation that hearing-assistance device 102 classifies automatically. Example types of environments include a "Speech-in-Noise" environment, a "Quiet" environment, a "Machine Noise" environment, and so on.

The focus sub-component for the wearer of hearing-assistance device 102 is a numerical value indicating an amount of time hearing-assistance device 102 has spent in a directional processing mode. The focus sub-component may be considered a measure of the wearer being able to hear sounds most important to the wearer. The focus sub-component may be scaled to be in a range used by the other sub-components. For instance, in some examples, the focus sub-component is equal to a percentage of time spent in a directional processing mode. For instance, in one such example, the focus sub-component is equal to a first value multiplied by 100, where the first value is equal to a second value divided by a third value; the second value being equal to an amount of time spent in a directional processing mode; the third value being equal to the total amount of time hearing-assistance device 102 is powered on. In an omni-directional mode, hearing-assistance device 102 does not selectively amplify or attenuate sounds from particular directions.

The sociability sub-component for the wearer of hearing-assistance device 102 is a numerical value indicating an amount of time hearing-assistance device 102 spent in auditory environments involving speech. The sociability sub-component may be considered a measure of time spent in conversation. The sociability sub-component may be scaled to be in a range used by the other sub-components. In some examples, the sociability sub-component is a percentage of time spent in social situations. For instance, in one such example, the sociability sub-component is equal to a first value multiplied by 100, where the first value is equal to a second value divided by a third value. In this example, the second value is equal to the amount of time spent in speech and speech in noise, and the third value is equal to the total amount of time that hearing-assistance device 102 is powered on.

The connectivity sub-component for the wearer of hearing-assistance device 102 is a numerical value indicating an amount of time hearing-assistance device 102 spent streaming audio data from devices that are wirelessly connective to hearing-assistance device 102. The connectivity sub-component may be considered a measure of time connecting with media. In some examples, the connectivity sub-component for the wearer is a measure of the amount of time spent streaming media (or the amount of time hearing-assistance device 102 spent maintaining connectivity for streaming media) relative to an amount of time, such as an amount of time associated with a maximum benefit attained from streaming media. This measure may be on a same scale (e.g., 0 to 100, 0 to 50, etc.) as the other sub-components. For instance, in one such example, the connectivity sub-component may be equal to a first value. In this example, the first value is equal to an amount of time spent streaming from a separate wireless device, up to a time associated with the maximum benefit attained from streaming media, divided by the time associated with the maximum benefit attained from streaming media.

Computing system 104 may determine the cognitive benefit measure based on the sub-components in various ways. For example, computing system 104 may determine the cognitive benefit measure based on an average or weighted average of the sub-components. In other words, the cognitive benefit measure may be an average of all the sub-component data, although the sub-components may be differentially weighted before averaging occurs. For example, the "connectivity" sub-component may be weighted more than the other measures because the expectation is that the connectivity sub-component typically yields a relatively small score because patients spend only a small percentage of the time streaming audio to their hearing aids. In some examples, computing system 104 determines the weights used in calculating the weighted average by normalizing the sub-components by a maximum benefit expected or predicted for each sub-component.

In some examples, computing system 104 scales the cognitive benefit measure (and the sub-components) by use time of hearing-assistance device 102. For example, if a user does not wear his or her hearing-assistance device on a given day, the cognitive benefit measure may not be calculated, but the more the user wears hearing-assistance device 102, the larger the cognitive benefit measure. This type of scaling may be intuitive for the user, and time spent using hearing-assistance device 102 may be one contributing factor to the cognitive benefit measure over which the user has the most control.

In some examples, computing system 104 may store historical cognitive benefit measures for the wearer of hearing-assistance device 102. For example, computing system 104 may store a cognitive benefit measure for each day or other time period. Additionally, computing system 104 may output data based on the historical cognitive benefit measures for display. In this way, the wearer of hearing-assistance device 102 may be able to track the wearer's cognitive benefit measures over time. For instance, the wearer of hearing-assistance device 102 may be able to track his or her progress.

As noted above, the cognitive benefit measure may be calculated based on data collected by hearing-assistance device 102. In some examples, hearing-assistance device 102 writes data to a data log. For example, hearing-assistance device 102 may store, in memory, counter data used for calculation of sub-components. For instance, hearing-assistance device 102 may store data indicating an amount of time hearing-assistance device 102 spent streaming media, an amount of time spent in a directional processing mode, and other values. Hearing-assistance device 102 may flush these values out to the data log on a period basis and may reset the values.

Hearing-assistance device 102 may communicate data in the data log to computing system 104. Computing system 104 may receive, from hearing-assistance device 102, the data from the data log. Computing system 104 may use the received information to determine the cognitive benefit measure.

Hearing-assistance device 102 may write the data to the data log on a periodic basis, e.g., once per time period. In some examples, the duration of the time period changes during the life cycle of hearing-assistance device 102. For example, hearing-assistance device 102 may write data to the data log once every 15 minutes during the first two years of use of hearing-assistance device 102 and once every 60 minutes following the first two years of use of hearing-assistance device 102. Because hearing-assistance device 102 sends data in the data log, as opposed to the live counter data, and hearing-assistance device 102 updates the data log on a periodic basis, the user may be able to access an updated cognitive benefit measures at least as often as the same periodic basis.

Furthermore, in some examples, in addition to determining a cognitive benefit measure (e.g., a brain score) for the wearer of hearing-assistance device 102, computing system 104 may use data collected by hearing-assistance device 102 to determine a body fitness measure for the wearer of hearing-assistance device 102. The body fitness measure for the wearer of hearing-assistance device 102 may be an indication of physical activity in which the wearer of hearing-assistance device 102 engages while wearing hearing-assistance device 102. Like the cognitive benefit measure, computing system 104 may determine the body fitness measure based on a plurality of sub-components. For instance, computing system 104 may determine the body fitness measure based on a "steps" sub-component, an "activity" sub-component, and a "move" sub-component. The "steps" component may indicate a number of steps (e.g., while walking or running) that the wearer of hearing-assistance device 102 has taken during a current scoring period. The "activity" sub-component may be a measure of vigorous activity in which the wearer of hearing-assistance device 102 has engaged during the current scoring period. The "move" sub-component may be based on a number time of intervals during the current scoring period in which the wearer of hearing-assistance device 102 moves for a given amount of time. The current scoring period may be an amount of time after which computing system 104 resets the cognitive benefit measure and/or the body fitness measure. For instance, the current scoring period may be one day, one week, or another time period. Thus, the cognitive benefit measure and the body fitness measure, and sub-components thereof, may be reset periodically or recurrently.

In some examples, computing system 104 may determine values of one or more of the sub-components of the cognitive benefit measure and the body fitness measure using goals. For instance, in one example with respect to the "steps" sub-component of the body fitness measure, the wearer of hearing-assistance device 103 may set a number of steps to take during a scoring period as a goal for the "steps" sub-component. In this example, computing system 104 may determine the value of the "steps" component based on the progress of the wearer of hearing-assistance device 102 during the scoring period toward the goal for the "steps" component. In some examples, such goals may be user-configurable. For example, computing system 104 may permit a user (e.g., the wearer of hearing-assistance device 102, a caregiver, a health care provider, or another person) to set the goals for particular wearers of hearing-assistance devices or for a population of patients. For example, wearers of hearing-assistance devices may be characterized (e.g., classified) using one or more of various techniques, such as artificial intelligence using demographic or medical information. In this example, goal(s) may be determined based upon such characterizations about wearers of hearing-assistance devices.

In some examples, computing system 104 may determine a "wellness" measure (e.g., a wellness score) for the wearer of hearing-assistance device 102. The wellness measure for the wearer of hearing-assistance device 102 may be an indication of an overall wellness of the wearer of hearing-assistance device 102. Computing system 104 may determine the wellness measure based on the cognitive benefit measure and the body fitness measure of the wearer of hearing-assistance device 102 for a scoring period. For instance, computing system 104 may determine the wellness measure as a weighted sum of the cognitive benefit measure, the body fitness measure, and possibly one or more other factors. In some examples, computing system 104 may determine the wellness measure as a multiplication product of the cognitive benefit measure and the body fitness measure.

In some examples, hearing-assistance device 102 calculates the body fitness measure and/or the wellness measure. In other examples, the body fitness measure and/or the wellness measure is calculated by one or more computing devices of computing system 104. For instance, in the example of FIG. 1, mobile device 106 or server device 108 may calculate the body fitness measure and/or the wellness measure. For ease of explanation, many of the examples of this disclosure describe computing system 104 calculating the body fitness measure and/or the wellness measure. However, these examples can be adapted to scenarios where hearing-assistance device 102 calculates the body fitness measure and/or wellness measure.

Computing system 104 may be configured to generate alerts based on one or more of a cognitive benefit measure, body fitness measure, a wellness measure of a wearer of hearing-assistance device 102, or a combination thereof An alert may alert the wearer of hearing-assistance device 102 or another person to the occurrence of a particular condition. In other words, computing system 104 may generate, based on the cognitive benefit measure, an alert to the wearer of hearing-assistance device 102 or another person. Computing system 104 may transmit an alert to a caregiver, healthcare professional, family member, or other person or persons. Computing system 104 may generate an alert when one or more of various conditions occur. For example, computing system 104 may generate an alert if computing system 104 detects a consistent downward trend in the wearer's body fitness measure, cognitive benefit measure, and/or wellness measure. In another example, computing system 104 may generate an alert if computing system 104 determines that the wearer's body fitness measure, cognitive benefit measure, and/or wellness measure are below one or more thresholds for a threshold amount of time (e.g., a particular number of days). In some examples, responsive to declaration of an alert, a therapy may be changed, or additional diagnostics may be performed, encouragement may be provided, or a communication may be initiated. In other examples, hearing-assistance device 102 may generate the alerts.

In some examples, hearing-assistance device 102 does not have a real time clock that keeps track of the current time and date. Not including such a real time clock in hearing-assistance device 102 may be advantageous for various reasons. For instance, because of the extreme size constraints on hearing-assistance device 102, the batteries of hearing-assistance device 102 may need to be very small. Maintaining a real time clock in hearing-assistance device 102 may consume a significant amount of power from the battery that may be better used for other purposes. Hearing-assistance device 102 may produce a clock signal that cycles at a given frequency so that hearing-assistance device 102 is able to track relative time. For instance, hearing-assistance device 102 may be able to count clock cycles to determine that a given amount of time (e.g., five minutes) has passed following a given clock cycle, but without a real-time clock hearing-assistance device 102 may not be equipped to relate that relative time to an actual time and date (e.g., 11:34 A.M. on Aug. 22, 2017). Moreover, maintaining a real time clock based on this clock signal may require hearing-assistance device 102 to continue the clock signal even while hearing-assistance device 102 is not in use, which may consume a significant amount of battery power.

However, several of the sub-components of the cognitive benefit measure and the body fitness measure are time-dependent. For example, the "use score" sub-component may be based on how much time the wearer of hearing-assistance device 102 uses the hearing-assistance device 102 during a scoring period. In another example, the "engagement" sub-component may be based at least in part on how much time the wearer of hearing-assistance device 102 engages in conversation during a scoring period and how much time the wearer of hearing-assistance device 102 uses hearing-assistance device 102 to stream audio media during the scoring period. Moreover, in some examples, computing system 104 may need to determine times associated with log data items received from hearing-assistance device 102 to determine whether the log data items are associated with a current scoring period.

This disclosure describes techniques that may overcome the problems associated with determining sub-components of the cognitive benefit measure and/or the body fitness measure in the absence of a real-time clock in hearing-assistance device 102. For example, hearing-assistance device 102 may maintain a data log that stores log data items, which may include sub-component data. The sub-component data may include data from which values of sub-components may, at least partially, be determined. For example, an inertial measurement unit (IMU) of hearing-assistance device 102 may periodically write data to the data log indicating the number of steps taken by the wearer of hearing-assistance device 102. In accordance with one or more techniques of this disclosure, hearing-assistance device 102 may receive timestamps from a computing device in computing system 104. For example, hearing-assistance device 102 may receive timestamps from mobile device 106. A timestamp may be a value that indicates a time. For instance, a timestamp may indicate a number of seconds that have passed since a fixed real time (e.g., since Jan. 1, 1970). When recording data (e.g., log data items) to the data log, hearing-assistance device 102 may include the timestamp in the log data item. For example, hearing-assistance device 102 may record a log data item in the data log indicating that the wearer of hearing-assistance device 102 has started using hearing-assistance device 102. In this example, hearing-assistance device 102 may include the timestamp in the log data item. In this example, computing system 104 may use this data recorded in the data log to determine the "use score" sub-component.

Thus, computing system 104 may send timestamps to hearing-assistance device 102. Additionally, computing system 104 may receive a plurality of log data items from hearing-assistance device 102. Each of the log data items may include log data and one of the timestamps sent to hearing-assistance device 102 by computing system 104. Computing system 104 may determine, based on the timestamps and the log data in the log data items, at least one of the cognitive benefit measure or the body fitness measure.

For instance, computing system 104 may use the timestamps in the log data items to determine which log data items are from a current scoring period and then only use log data in the log data items from the current scoring period when determining values of the sub-components of the cognitive benefit measure and/or body fitness measure.

Hearing-assistance device 102 may receive timestamps from computing system 104 in response to one or more of various events. For example, hearing-assistance device 102 may send a timestamp request to computing system 104 when preparing to write data to the data log. In some examples, hearing-assistance device 102 may periodically request timestamps from computing system 104. In some examples, computing system 104 may be configured to periodically send timestamps to hearing-assistance device 102 on an asynchronous basis. That is, in this example, it may not be necessary for hearing-assistance device 102 to send a request to computing system 104 for timestamps. For instance, computing system 104 may send a timestamp to hearing-assistance device 102 once every 60 seconds, 30 seconds, or other time period. In this example, hearing-assistance device 102 may store the timestamp (potentially overwriting a previous version of the timestamp) and then include a copy of the timestamp in a log data item when storing the log data item to the data log. Because exact precision may not be necessary when determining values of sub-components of the cognitive benefit measure and the body fitness measure, including an exactly correct time in a log data item may be unnecessary. Thus, the cycle time for hearing-assistance device 102 receiving timestamps may be set slow enough that an amount of energy consumed by wireless receiving and writing the timestamps to memory may be less than the amount of energy that would be consumed by hearing-assistance device 102 maintaining its own real time clock, while allowing for reasonable accuracy.

Figure 2:
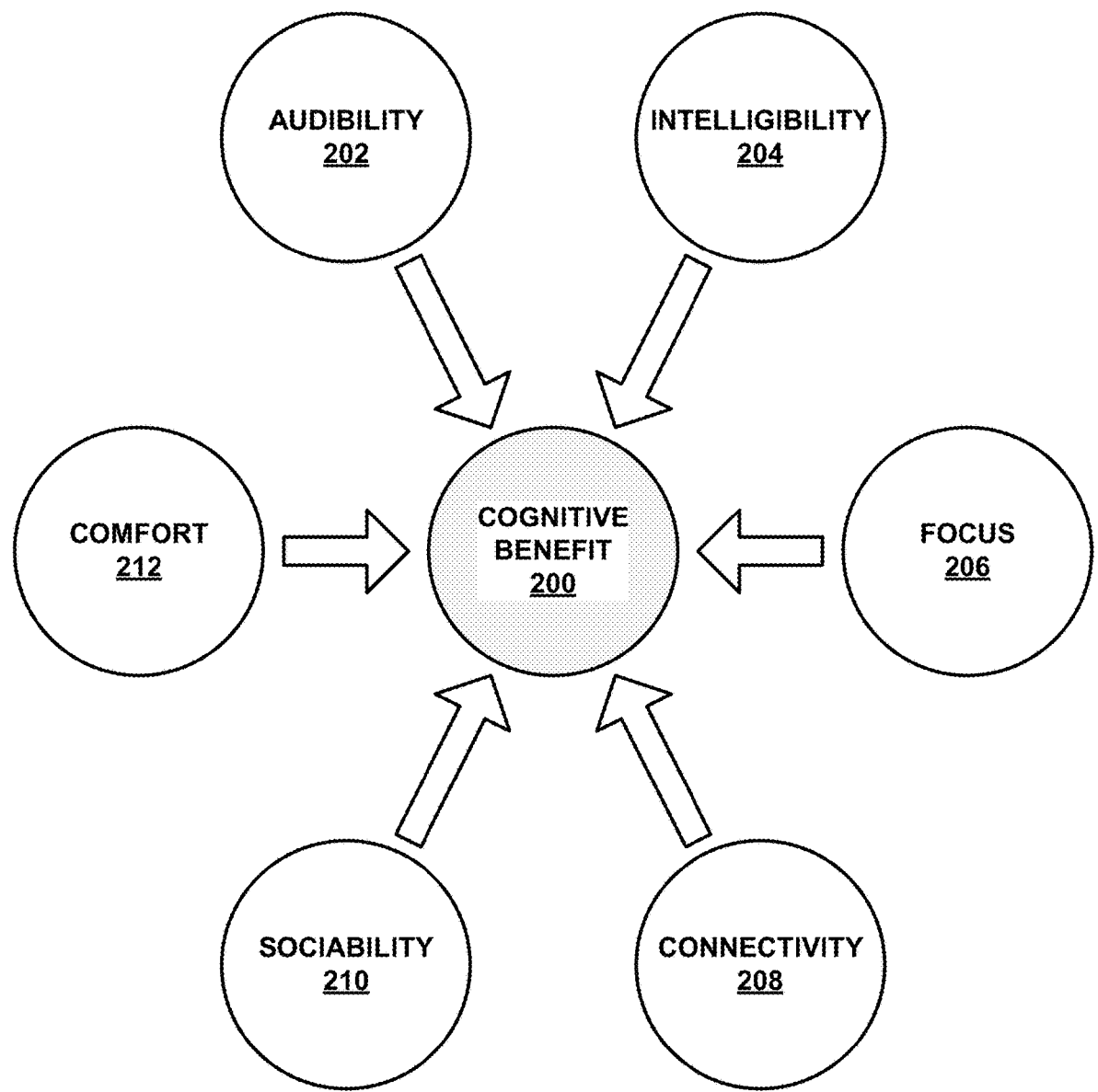
FIG. 2 is a conceptual diagram illustrating contributions of sub-components to a cognitive benefit measure, in accordance with one or more aspects of this disclosure.

FIG. 2 is a conceptual diagram illustrating contributions of sub-components to a cognitive benefit measure 200, in accordance with one or more aspects of this disclosure. Consistent with the example above, cognitive benefit measure 200 may be determined based on an audibility sub-component 202, an intelligibility sub-component 204, a focus sub-component 206, a connectivity sub-component 208, a sociability sub-component 210, and a comfort sub-component 212. Thus, in the example of FIG. 2, six sub-components (white circles) contribute to the composite cognitive benefit measure (shaded circle); the relationship is denoted by the arrows.

In some examples, computing system 104 may output a graphical user interface (GUI) for display on a display screen. For example, mobile device 106 may output the GUI for display on a display screen of mobile device 106. In another example, server device 108 may generate data defining a webpage comprising the GUI and send the data mobile device 106 or another computing device (e.g., a personal computer) for rendering for display by a web browser application. The GUI may include content similar to that shown in FIG. 2. In response to receiving an indication of user input to select a circle corresponding to a given sub-component, computing system 104 may output for display, information about what is being measured in the given sub-component. However, in some examples, computing system 104 does not cause actual calculations for the sub-components to be displayed. For example, the "sociability" sub-component is a numerical value indicating a measure of the amount of time a wearer of hearing-assistance device 102 spends in social situations, but the wearer is not privy to the fact that this measure is calculated as the amount of time an automatic environmental classification system of hearing-assistance device 102 detects speech.

Figure 3:
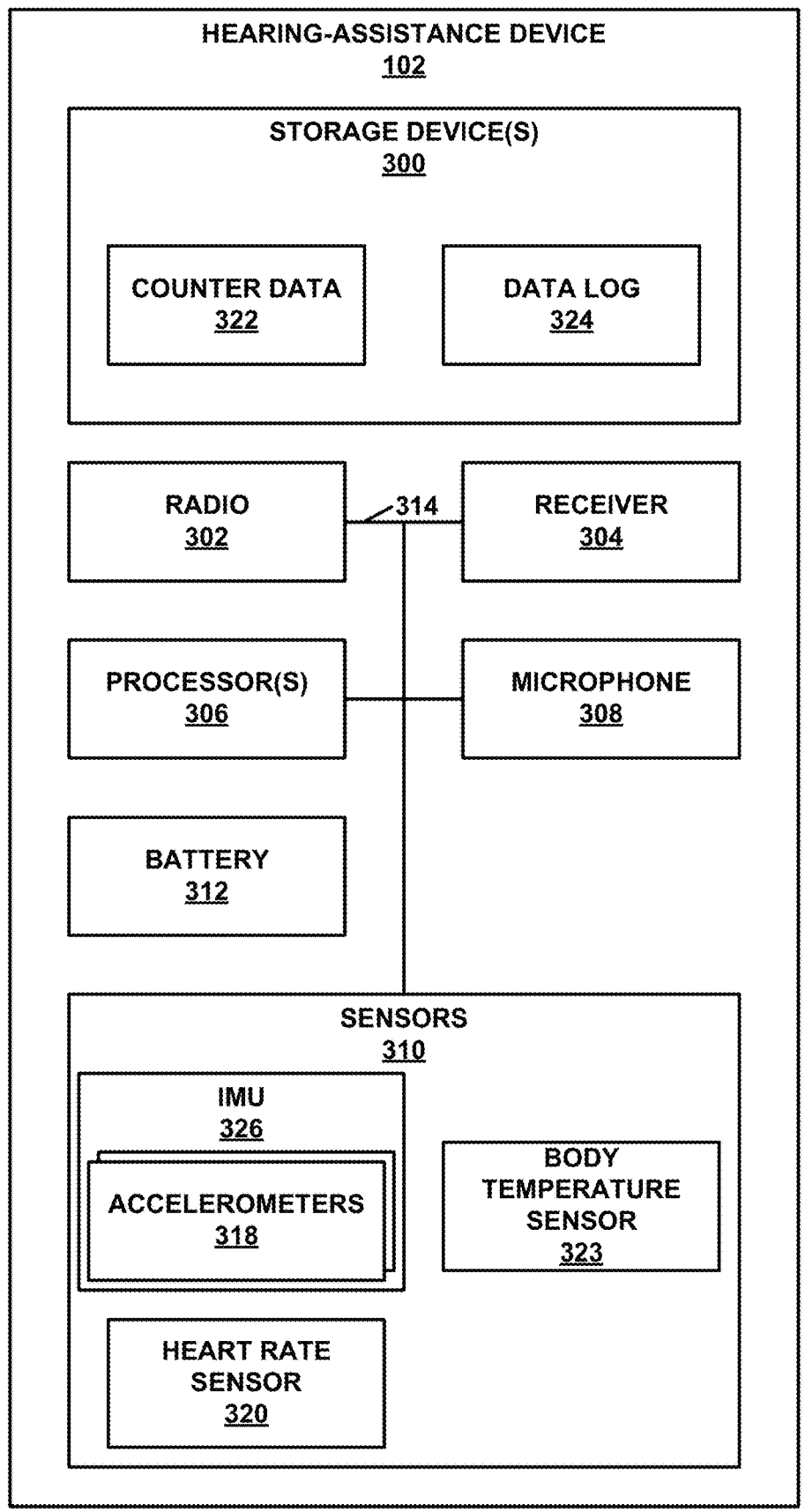
FIG. 3 is a block diagram illustrating example components of a hearing-assistance device, in accordance with one or more aspects of this disclosure.

FIG. 3 is a block diagram illustrating example components of hearing-assistance device 102, in accordance with one or more aspects of this disclosure. In the example of FIG. 3, hearing-assistance device 102 comprises one or more storage device(s) 300, a radio 302, a receiver 304, one or more processor(s) 306, a microphone 308, a set of sensors 310, a battery 312, and one or more communication channels 314. Communication channels 314 provide communication between storage device(s) 300, radio 302, receiver 304, processor(s) 306, a microphone 308, and sensors 310. Components 300, 302, 304, 306, 308, and 310 may draw electrical power from battery 312.

In the example of FIG. 3, sensors 310 include one or more accelerometers 318. Furthermore, in examples such as that of FIG. 3, an inertial measurement unit (IMU) 326 includes one or more of accelerometers 318. The IMU 326 may use signals generated by accelerometers 318 for various purposes. For example, the IMU 326 may use the signals generated by accelerometers 318 to count the number of steps that a wearer of hearing assistance device 102 has taken.

Additionally, in the example of FIG. 3, sensors 310 also include a heart rate sensor 320 and a body temperature sensor 323. In other examples, hearing-assistance device 102 may include more, fewer, or different components. For instance, in other examples, hearing-assistance device 102 does not include particular sensors shown in the example of FIG. 3. In some examples, heart rate sensor 320 comprises a visible light sensor and/or a pulse oximetry sensor.

Storage device(s) 300 may store data. Storage device(s) 300 may comprise volatile memory and may therefore not retain stored contents if powered off. Examples of volatile memories may include random access memories (RAM), dynamic random access memories (DRAM), static random access memories (SRAM), and other forms of volatile memories known in the art. Storage device(s) 300 may further be configured for long-term storage of information as non-volatile memory space and retain information after power on/off cycles. Examples of non-volatile memory configurations may include magnetic hard discs, optical discs, floppy discs, flash memories, or forms of electrically programmable memories (EPROM) or electrically erasable and programmable (EEPROM) memories.

Radio 302 may enable hearing-assistance device 102 to send data to and receive data from one or more other computing devices. For example, radio 302 may enable hearing-assistance device 102 to send data to and receive data from mobile device 106 (FIG. 1). Radio 302 may use one or more of various types of wireless technology to communicate. For instance, radio 302 may use Bluetooth, 3G, 4G, 4G LTE, ZigBee, WiFi, Near-Field Magnetic Induction (NFMI), or another communication technology.

Receiver 304 comprises one or more speakers for generating audible sound. Microphone 308 detects incoming sound and generates an electrical signal (e.g., an analog or digital electrical signal) representing the incoming sound. Processor(s) 306 may process the signal generated by microphone 308 to enhance, amplify, or cancel-out particular channels within the incoming sound. Processor(s) 306 may then cause receiver 304 to generate sound based on the processed signal. In some examples, processor(s) 306 include one or more digital signal processors (DSPs).

Processor(s) 306 may cause radio 302 to transmit one or more of various types of data. For example, processor(s) 306 may cause radio 302 to transmit data to computing system 104. Furthermore, radio 302 may receive audio data from computing system 104 and processor(s) 306 may cause receiver 304 to output sound based on the audio data.

In some examples, hearing-assistance device 102 is a "plug-n-play" type of device. In some examples, hearing-assistance device 102 is programmable to help the user manage things like wind noise. Furthermore, in some examples, hearing-assistance device 102 comprises a custom earmold or a standard receiver module at the end of a RIC cable. The additional volume in a custom earmold may allow room for components such as sensors (accelerometers, heartrate monitors, temp sensors), a woofer-tweeter, (providing richer sound for music aficionados), and an acoustic valve that provides occlusion when desired. In some examples, a six conductor RIC cable is used for in hearing-assistance devices with sensors, woofer-tweeters, and/or acoustic valves.

In the example of FIG. 3, storage device(s) 300 may store counter data 322 and a data log 324. Counter data 322 may include actively updated data used for determining sub-components of a cognitive benefit measure. For example, hearing-assistance device 102 may store data indicating an amount of time hearing-assistance device 102 spent streaming media, an amount of time spent in a directional processing mode, and other values. Processor(s) 306 may update counter data 322 at a more frequent rate than data log 324. Processor(s) may flush values from counter data 322 out to data log 324 on a period basis and may reset counter data 322. Additionally, processor(s) 306 may cause radio 302 to send data in data log 324 to computing system 104. For instance, processor(s) 306 may cause radio 302 to send data in data log 324 to computing system 104 in response to radio 302 receiving a request for the data from computing system 104.

Figure 4:
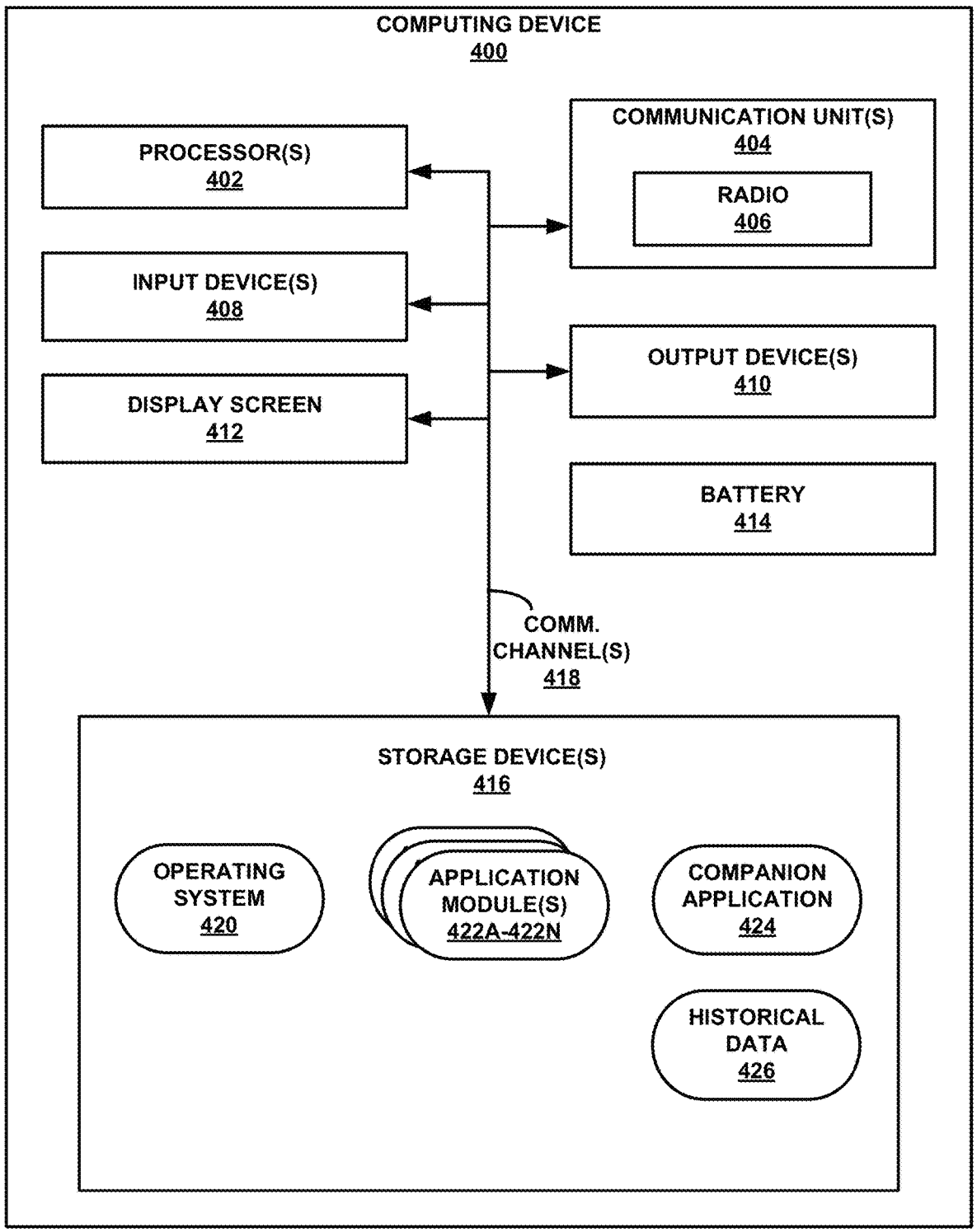
FIG. 4 is a block diagram illustrating example components of a mobile computing device, in accordance with one or more aspects of this disclosure.

FIG. 4 is a block diagram illustrating example components of computing device 400, in accordance with one or more aspects of this disclosure. FIG. 4 illustrates only one particular example of computing device 400, and many other example configurations of computing device 400 exist. Computing device 400 may be a computing device in computing system 104 (FIG. 1). For instance, computing device 400 may be mobile device 106 or server device 108.

As shown in the example of FIG. 4, computing device 400 includes one or more processors 402, one or more communication units 404, one or more input devices 408, one or more output devices 410, a display screen 412, a battery 414, one or more storage devices 416, and one or more communication channels 418. Computing device 400 may include many other components. For example, computing device 400 may include physical buttons, microphones, speakers, communication ports, and so on. Communication channel(s) 418 may interconnect each of components 402, 404, 408, 410, 412, and 416 for inter-component communications (physically, communicatively, and/or operatively). In some examples, communication channel(s) 418 may include a system bus, a network connection, an inter-process communication data structure, or any other method for communicating data. Battery 414 may provide electrical energy to components 402, 404, 408, 410, 412 and 416.

Storage device(s) 416 may store information required for use during operation of computing device 400. In some examples, storage device(s) 416 have the primary purpose of being a short term and not a long-term computer-readable storage medium. Storage device(s) 416 may be volatile memory and may therefore not retain stored contents if powered off. Storage device(s) 416 may further be configured for long-term storage of information as non-volatile memory space and retain information after power on/off cycles. In some examples, processor(s) 402 on computing device 400 read and may execute instructions stored by storage device(s) 416.

Computing device 400 may include one or more input device(s) 408 that computing device 400 uses to receive user input. Examples of user input include tactile, audio, and video user input. Input device(s) 408 may include presence-sensitive screens, touch-sensitive screens, mice, keyboards, voice responsive systems, microphones or other types of devices for detecting input from a human or machine.

Communication unit(s) 404 may enable computing device 400 to send data to and receive data from one or more other computing devices (e.g., via a communications network, such as a local area network or the Internet). In some examples, communication unit(s) 404 may include wireless transmitters and receivers that enable computing device 400 to communicate wirelessly with the other computing devices. For instance, in the example of FIG. 4, communication unit(s) 404 include a radio 406 that enables computing device 400 to communicate wirelessly with other computing devices, such as hearing-assistance device 102 (FIG. 1, FIG. 3). Examples of communication unit(s) 404 may include network interface cards, Ethernet cards, optical transceivers, radio frequency transceivers, or other types of devices that are able to send and receive information. Other examples of such communication units may include Bluetooth, 3G, and WiFi radios, Universal Serial Bus (USB) interfaces, etc. Computing device 400 may use communication unit(s) 404 to communicate with one or more hearing-assistance devices (e.g., hearing-assistance device 102 (FIG. 1, FIG. 3)). Additionally, computing device 400 may use communication unit(s) 404 to communicate with one or more other remote devices (e.g., server device 108 (FIG. 1)).

Output device(s) 410 may generate output. Examples of output include tactile, audio, and video output. Output device(s) 410 may include presence-sensitive screens, sound cards, video graphics adapter cards, speakers, liquid crystal displays (LCD), or other types of devices for generating output.

Processor(s) 402 may read instructions from storage device(s) 416 and may execute instructions stored by storage device(s) 416. Execution of the instructions by processor(s) 402 may configure or cause computing device 400 to provide at least some of the functionality ascribed in this disclosure to computing device 400. As shown in the example of FIG. 4, storage device(s) 416 include computer-readable instructions associated with operating system 420, application modules 422A-422N (collectively, "application modules 422"), and a companion application 424. Additionally, in the example of FIG. 4, storage device(s) 416 may store historical data 426.

Execution of instructions associated with operating system 420 may cause computing device 400 to perform various functions to manage hardware resources of computing device 400 and to provide various common services for other computer programs. Execution of instructions associated with application modules 422 may cause computing device 400 to provide one or more of various applications (e.g., "apps," operating system applications, etc.). Application modules 422 may provide particular applications, such as text messaging (e.g., SMS) applications, instant messaging applications, email applications, social media applications, text composition applications, and so on.

Execution of instructions associated with companion application 424 may cause computing device 400 to perform one or more of various functions described in this disclosure with respect to computing system 104 (FIG. 1). For example, execution of instructions associated with companion application 424 may cause computing device 400 to configure radio 406 to wirelessly receive data from hearing-assistance device 102 (FIG. 1; FIG. 3). Additionally, execution of instructions of companion application 424 may cause computing device 400 to determine a cognitive benefit measure, a body fitness measure, and/or a wellness measure for a wearer of hearing-assistance device 102 and output an indication of the cognitive benefit measure, the body fitness measure, and/or the wellness measure. Although not explicitly recited here for the sake of brevity, instructions associated with companion application 424 may cause computing device 400 to perform one or more of various other actions of computing system 104. In some examples, companion application 424 is an instance of a web application or server application. In some examples, such as examples where computing device 400 is a mobile device, companion application 424 may be a native application.

In some examples, a GUI of companion application 424 has a plurality of different sections, that may or may not appear concurrently. For example, the GUI of companion application 424 may include a section for controlling the intensity of sound generated by (e.g., the volume of) hearing-assistance device 102, a section for controlling how hearing-assistance device 102 attenuates wind noise, a second for finding hearing-assistance device 102 if lost, and so on. Additionally, the GUI of companion application 424 may include a cognitive benefit section that displays data regarding a cognitive benefit measure for the wearer of hearing-assistance device 102. In some examples, the cognitive benefit section of companion application 424 displays a diagram similar to that shown in the example of FIG. 2 or the example of FIG. 8. Additionally, the GUI of companion application 424 may include a body fitness measure section that displays data regarding a body fitness measure for the wearer of hearing-assistance device 102. In some examples, the body fitness measure section of companion application 424 displays a diagram similar to the example of FIG. 9, described below. The GUI of companion application 424 may also include a wellness measure section that displays data regarding a wellness measure for the wearer of hearing-assistance device 102. In some examples, the wellness measure section of companion application 424 displays a diagram similar to the example of FIG. 10, described below.

In some examples, companion application 424 may request data for calculating a cognitive benefit measure or body fitness measure from hearing-assistance device 102 each time mobile device 106 receives an indication of user input to navigate to the cognitive benefit section or body fitness measure section of companion application 424. In this way, a wearer of hearing-assistance device 102 may get real-time confirmation that companion application 424 is communicating with hearing-assistance device 102, that the data displayed are current, and may ensure that the wireless transfer of the data-log data does not interrupt or interfere with other processes in companion application 424, or on computing device 400 device. Furthermore, requesting data from hearing-assistance device 102 only when computing device 400 receive an indication of user input to navigate to the cognitive benefit section, the body fitness measure section, or the wellness measure section of companion application 424 may reduce demands on a battery (e.g., battery 312 of FIG. 3) of hearing-assistance device 102 (FIG. 1; FIG. 3), relative to computing device 400 requesting the data from hearing-assistance device 102 on a periodic basis.

Companion application 424 may store one or more of various types of data as historical data 426. Historical data 426 may comprise a database for storing historic data related to cognitive benefit. For example, companion application 424 may store, in historical data 426, cognitive benefit measures, body fitness measures, sub-component values, data from hearing-assistance device 102, and/or other data. Companion application 424 may retrieve data from historical data 426 to generate a GUI for display of past cognitive benefit measures, body fitness measures, and wellness measures of the wearer of hearing-assistance device 102.

Figure 5:
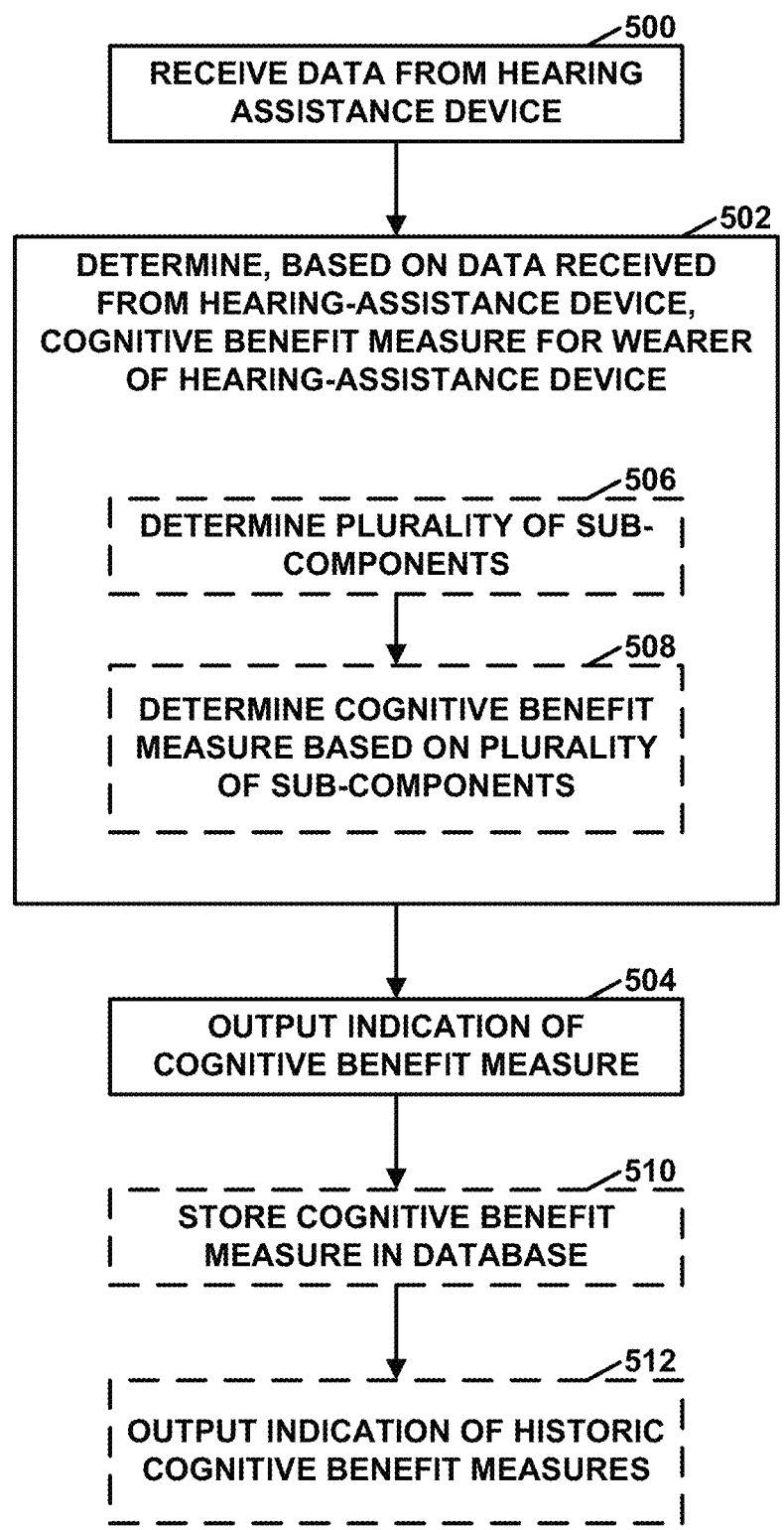
FIG. 5 is a flowchart illustrating an example operation of a computing system, in accordance with one or more aspects of this disclosure.

FIG. 5 is a flowchart illustrating an example operation of computing system 104, in accordance with one or more aspects of this disclosure. The flowcharts of this disclosure are provided as examples. In other examples, operations shown in the flowcharts may include more, fewer, or different actions, or actions may be performed in different orders or in parallel.

In the example of FIG. 5, computing system 104 may receive data from hearing-assistance device 102 (500). For example, computing system 104 may receive data from hearing-assistance device 102 in response to computing system 104 sending a request for the data to hearing-assistance device 102. In some examples, computing system 104 receives an indication of user input to access a cognitive benefit section of a GUI of a software application (e.g., companion application 424) running on computing system 104. In this example, in response to receiving the indication of user input, computing system 104 sends a request to hearing-assistance device 102 and computing system 104 receives the data from hearing-assistance device 102 in response to the request.

Additionally, computing system 104 may determine, based on the data received from hearing-assistance device 102, a cognitive benefit measure for a wearer of hearing-assistance device 102 (502). The cognitive benefit measure may be an indication of a change of a cognitive benefit of the wearer of hearing-assistance device 102 attributable to use of hearing-assistance device 102 by the wearer of hearing-assistance device 102. In some examples, computing system 104 may scale the cognitive benefit measure based on an amount of time the wearer spends wearing hearing-assistance device 102.

Furthermore, in the example of FIG. 5, computing system 104 may output an indication of the cognitive benefit measure (504). For example, computing system 104 may output a GUI for display that includes a numerical value indicating the cognitive benefit measure. In some examples, to output the indication of the cognitive benefit measures, computing system 104 may send to hearing-assistance device 102 audio data that represents the cognitive benefit measure in audible form.

As shown in the example of FIG. 5, computing system 104 may, as part of determining the cognitive benefit measure for the wearer of hearing-assistance device 102, determine a plurality of sub-components of the cognitive benefit measure (506). Additionally, computing system 104 may determine the cognitive benefit measure based on the plurality of sub-components of the cognitive benefit measure (508). For example, computing system 104 may determine a weighted average of the plurality of sub-components to determine the cognitive benefit measure.

As part of determining the plurality of sub-components, computing system 104 may determine an "audibility" sub-component, an "intelligibility" sub-component, a "comfort" sub-component, a "focus" sub-component, a "sociability" sub-component, and a "connectivity" sub-component. For example, computing system 104 may determine an audibility sub-component that is a measure of the improvement in audibility provided to the wearer by hearing-assistance device 102. For instance, the audibility sub-component may indicate a measure of detected sounds that are amplified sounds. In this example, each of the detected sounds is a sound detected by hearing-assistance device 102. Furthermore, in this example, each respective amplified sound is a sound that was amplified by hearing-assistance device 102 because the intensity of the sound was below an audibility threshold of the wearer of hearing-assistance device 102. In this example, the audibility threshold of the wearer of hearing-assistance device 102 is an intensity level below which the wearer of hearing-assistance device 102 is unable to reliably hear the sound.

In some examples, computing system 104 may determine an intelligibility sub-component that indicates a measure of an improvement in speech understanding provided by hearing-assistance device 102. Furthermore, in some examples, computing system 104 may determine a comfort sub-component that indicates a measure of noise reduction provided by hearing-assistance device 102. In some examples, computing system 104 may determine a focus sub-component that indicates a measure of time hearing-assistance device 102 spends in directional processing modes. In this example, each of the respective directional processing modes selectively attenuates off-axis, unwanted sounds. Furthermore, in some examples, computing system 104 may determine a sociability sub-component that indicates a measure of time spent in auditory environments involving speech. In some examples, computing system 104 may determine a connectivity sub-component that indicates a measure of an amount of time hearing-assistance device 102 spent streaming media from devices connected wirelessly to hearing-assistance device 102.

In some examples, as part of determining the plurality of sub-components, computing system 104 may determine a "use score" sub-component, an "engagement score" sub-component, and an "active listening" sub-component. In such examples, computing system 104 may determine the cognitive benefit measure (e.g., a brain score) as a weighted sum of the "use score" sub-component, the "engagement score" sub-component, and the "active listening" sub-component. For instance, computing system 104 may determine the cognitive benefit measure such that a first percentage (e.g., 40%) of the cognitive benefit measure is based on the "use score" sub-component, a second percentage (e.g., 40%) of the cognitive benefit measure is based on the "engagement score" sub-component, and a third percentage (e.g., 20%) of the cognitive benefit measure is based on the "active listening" sub-component.

In such examples, the "use score" sub-component may be based on an amount of time during a scoring period that the wearer of hearing-assistance device 102 has used hearing-assistance device 102. The wearer of hearing-assistance device 102 may be considered to be using hearing-assistance device 102 when hearing-assistance device 102 is in the wearer's ear and turned on. In some examples, hearing-assistance device 102 may determine whether hearing-assistance device 102 is in the wearer's ear based on one or more of various signals generated by sensors 310 (FIG. 3). For instance, hearing-assistance device 102 may determine whether hearing-assistance device 102 is in the wearer's ear based on a pattern of motion signals generated by accelerometers 318 (FIG. 3), based on a body temperature signal from body temperature sensor 323, and/or based on a heart rate signal from heart rate sensor 320. In some examples, computing system 104 may determine the "use score" based on a comparison of an in-use time to a time goal. The in-use time may indicate the amount of time that hearing-assistance device 102 is in the wearer's ear and turned on. The time goal may be a predetermined amount of time (e.g., 12 hours). Thus, in one example, computing system 104 may determine the value of the "use score" sub-component based on the in-use time during the current scoring period divided by the time goal, multiplied by a maximum value of the "use score" subcomponent. Thus, in this example, if the time goal is 12 hours during the current scoring period, the maximum value of the "use score" subcomponent is 40 and the in-use time is 12 hours, computing system 104 may determine that the value of the "use score" sub-component is equal to 40.

In some examples, hearing-assistance device 102 may record log data items in data log 324 that include timestamps of when the wearer started and stopped wearing hearing-assistance device 102.

The "engagement score" sub-component may be a measure of how much the wearer of hearing-assistance device 102 participates in activities involving aural engagement during a scoring period. Example types of activities involving aural engagement include engaging in conversation, streaming audio data (e.g., streaming music, streaming audio data from television or a cinema), and other activities that involve the wearer of hearing-assistance device 102 actively listening to sounds.

In examples where the value of the "engagement score" sub-component is based on the wearer of hearing-assistance device 102 engaging in conversation, hearing-assistance device 102 may run an acoustic classifier that classifies sounds detected by hearing-assistance device 102. For example, the acoustic classifier may determine whether the current sound detected by hearing-assistance device 102 is silent, speaking and quiet, speaking with noise, music, and wind. In other examples, the acoustic classifier may classify the detected sounds into other categories.

In some examples, computing system 104 may determine the value of the "engagement score" sub-component based at least in part on an amount of time that the sound detected by hearing-assistance device 102 is classified into a speech category. Hearing-assistance device 102 may record transitions between categories as log data items in data log 324. In some examples, computing system 104 may determine the value of the "engagement score" sub-component based at least in part of a number of times that hearing-assistance device 102 determines during the current scoring period that the type of sound detected by hearing-assistance device 102 transitions to a speech category from another type of sound. For instance, computing system 104 may determine the "engagement score" sub-component based on the progress of the wearer of hearing-assistance device 102 toward a goal of a particular amount of time that sound detected by hearing-assistance device 102 is classified into a speech category Furthermore, in some examples, computing system 104 may determine the "engagement score" sub-component based on multiple activities involving aural engagement. For example, computing system 104 may determine a first component of the "engagement score" sub-component based on engagement in conversation and a second component of the "engagement score" sub-component based on streaming audio data. In some examples, hearing-assistance device 102 may record log data items in data log 324 that include timestamps of when hearing-assistance device 102 started and stopped streaming media data. In this example, the first factor may be determined in the same manner as the "sociability" sub-component described elsewhere in this disclosure and the second factor may be determined in the same manner as the "connectivity" sub-component described elsewhere in this disclosure. In this example, a first percentage (e.g., 80%) of the "engagement score" sub-component may be based on the first factor and a second percentage (e.g., 20%) of the "engagement score" sub-component may be based on the second factor. For instance, computing system 104 may determine the "engagement score" as a weighted sum of the first and second factors.

The "active listening" sub-component may be determined based on exposure of the wearer of hearing-assistance device 102 to a plurality of different acoustic environments during a current scoring period. For example, hearing-assistance device 102 may determine whether the sound detected by hearing-assistance device 102 is associated with particular types of acoustic environments. Example types of acoustic environments may include speech, speech with noise, quiet, machine noise, and music. In some examples, hearing-assistance device 102 may record log data items in data log 324 indicating transitions between acoustic environments and timestamps associated with such transitions. Computing system 104 may increment, based on the log data, the "active listening" sub-component for each different type of acoustic environment that hearing-assistance device 102 detects during a scoring period. For instance, computing system 104 may increment the "active listening" sub-component by $x_1$ points (e.g., 4 points) for exposure to a first acoustic environment, $x_2$ for exposure to a second acoustic environment, and so on, where $x_1$, $x_2$, ... $x_4$ are the same value or two or more different values. In some examples, computing system 104 may also or alternatively determine the value of the "active listening" sub-component based on progress of the wearer of hearing-assistance device 102 during the current scoring period toward a goal for the "active listening" sub-component. The goal for the "active listening" sub-component may be an amount of time that hearing-assistance device 102 spends performing a specified function, such as processing speech, processing sound in a directional mode, etc. In another example, the goal for the "active listening" sub-component may be a number of acoustic environments that the wearer of hearing-assistance device 102 is to experience during the scoring period.

Furthermore, in some examples, as shown in FIG. 5, computing system 104 may store the cognitive benefit measure in a database (e.g., historical data 426 (FIG. 4)) of historical cognitive benefit measures for the wearer of hearing-assistance device 102 (510). Additionally, computing system 104 may output an indication of the historical cognitive benefit measures (512). For example, computing system 104 may output a graph for display indicating cognitive benefit measures over time for the wearer of hearing-assistance device 102. In some examples, the historical information may be based on an hour, day, week, month, and/or year, and may be presented as discrete values or a trend (e.g., graph). In some examples, to output the indication of the historical cognitive benefit measures, computing system 104 may send to hearing-assistance device 102 audio data that represents the historical cognitive benefit measures in audible form.

Figure 6:
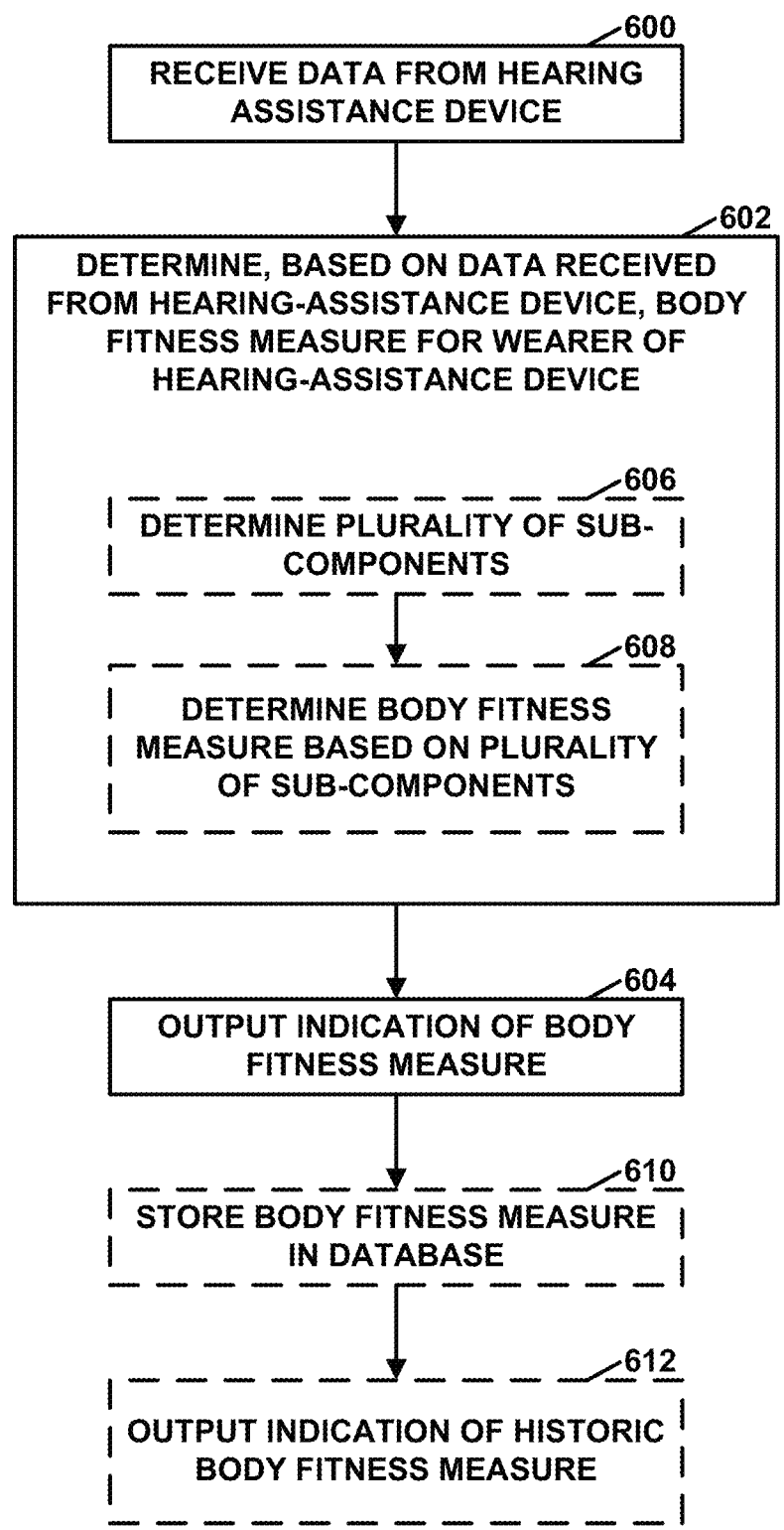
FIG. 6 is a flowchart illustrating an example operation to compute a body fitness measure in accordance with one or more aspects of this disclosure.

FIG. 6 is a flowchart illustrating an example operation to compute a body fitness measure in accordance with one or more aspects of this disclosure. In the example of FIG. 6, computing system 104 may receive data from hearing-assistance device 102 (600). For example, computing system 104 may receive data from hearing-assistance device 102 in response to computing system 104 sending a request for the data to hearing-assistance device 102. In some examples, computing system 104 receives an indication of user input to access a body fitness measure section of a graphical user interface (GUI) of a software application (e.g., companion application 424) running on computing system 104. In this example, in response to receiving the indication of user input, computing system 104 sends a request to hearing-assistance device 102 and computing system 104 receives the data from hearing-assistance device 102 in response to the request. In some examples, computing system 104 may receive a copy of data in data log 324 (FIG. 3) in accordance with any of the examples provided elsewhere in this disclosure.

Additionally, computing system 104 may determine, based on the data received from hearing-assistance device 102, a body fitness measure for the wearer of hearing-assistance device 102 (602). The body fitness measure may be an indication of a level of physical activity in which the wearer of hearing-assistance device 102 has engaged during a scoring period while wearing hearing-assistance device 102. In some examples, computing system 104 may scale the body fitness measure based on an amount of time the wearer of hearing-assistance device 102 spends wearing hearing-assistance device 102.

Figure 9:
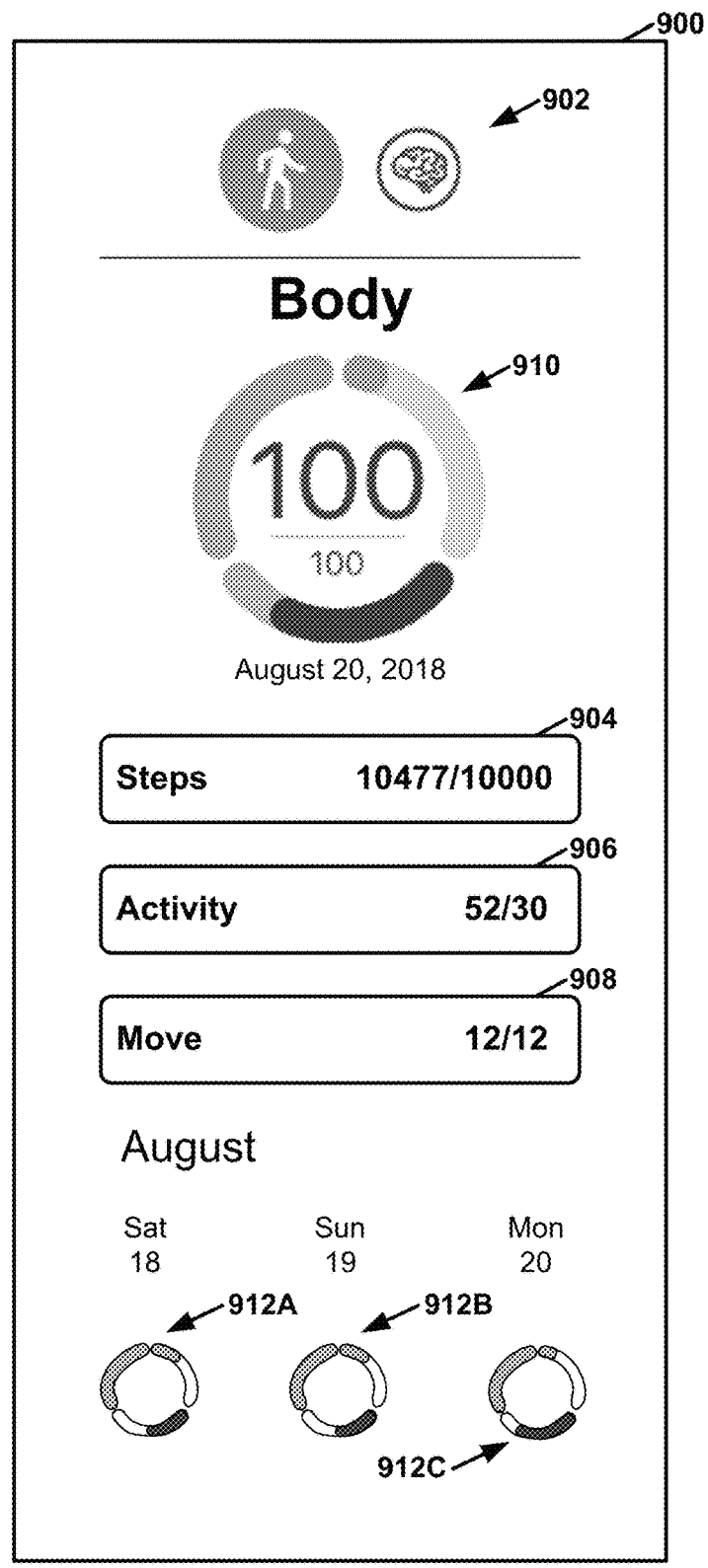
FIG. 9 is an example GUI for display of a body fitness measure in accordance with one or more aspects of this disclosure.

Furthermore, in the example of FIG. 6, computing system 104 may output an indication of the body fitness measure (604). For example, computing system 104 may output a GUI for display that includes a numerical value indicating the body fitness measure. FIG. 9, described in detail below, is an example GUI for display of the body fitness measure. In some examples, to output the indication of the body fitness measure, computing system 104 may send to hearing-assistance device 102 audio data that represents the body fitness measure in audible form.

As shown in the example of FIG. 6, computing system 104 may, as part of determining the body fitness measure for the wearer of hearing-assistance device 102, determine a plurality of sub-components of the body fitness measure (606). Additionally, computing system 104 may determine the body fitness measure based on the plurality of sub-components of the body fitness measure (608). For example, computing system 104 may determine a weighted average of the plurality of sub-components to determine the body fitness measure.

As part of determining the plurality of sub-components, computing system 104 may determine a "steps" sub-component, an "activity" sub-component, and a "move" sub-component. The "steps" sub-component may be based on a number of steps (e.g., while walking or running) that the wearer of hearing-assistance device 102 has taken during the current scoring period. In some examples, computing system 104 may determine a value of the "steps" sub-component based on the progress during the current scoring period of the wearer of hearing-assistance device 102 toward a goal for the "steps" sub-component. Furthermore, in some examples, IMU 326 determines the number of steps and hearing-assistance device 102 writes data indicating the number of steps to data log 324. In some examples, hearing-assistance device 102 stores timestamps with the number of steps.

The "activity" sub-component may be a measure of vigorous activity in which the wearer of hearing-assistance device 102 has engaged during the current scoring period. For example, computing system 104 may increment the "activity" sub-component in response to determining that the wearer of hearing-assistance device 102 has performed a vigorous activity. In some examples, computing system 104 may determine a value of the "activity" sub-component based on the progress during the current scoring period of the wearer of hearing-assistance device 102 toward meeting a goal for the "activity" sub-component. In such examples, the goal for the "activity" sub-component may be defined as a number of vigorous activities or amount of time engaged in vigorous activities to be performed during the current scoring period.

Computing system 104 or hearing-assistance device 102 may determine whether the wearer of hearing-assistance device 102 has performed a vigorous activity in one or more of various ways. For example, computing system 104 or hearing-assistance device 102 may determine that the wearer of hearing-assistance device 102 has performed a vigorous activity if computing system 104 has taken more than a given number of steps in a given amount of time. For instance, computing system 104 or hearing-assistance device 102 may assume that the wearer of hearing-assistance device 102 has run (or engaged in an activity more vigorous than a brisk walk) if the wearer of hearing-assistance device 102 has taken more than a threshold number of steps within a given time period.

Hearing-assistance device 102 may store one or more of various types of data to data log 324 to enable computing system 104 to determine the "activity" sub-component. For example, IMU 326 may output the number of steps taken during a given period. For instance, for every minute, IMU 326 may output the number of steps taken during that minute. Hearing-assistance device 102 may write a log data item including a timestamp to data log 324 if the number of steps taken during the given period is greater than a threshold associated with vigorous activity.

The "move" sub-component may be based on a number time of intervals during the current scoring period in which the wearer of hearing-assistance device 102 moves for a given amount of time. For example, computing system 104 may determine the "move" sub-component as a number of hours during a day in which the wearer of hearing-assistance device 102 was actively moving for more than 1 minute. In some examples, computing system 104 may determine the "move" sub-component based on progress of the wearer of hearing-assistance device 102 during the current scoring period toward a goal for the "move" sub-component. In such examples, the goal for the "move" sub-component may be defined as a given number of time intervals during the current scoring period in which the wearer of hearing-assistance device 102 moves for the given amount of time.

Hearing-assistance device 102 may store one or more of various types of data to data log 324 to enable computing system 104 to determine the "move" sub-component. For instance, in one example, hearing-assistance device 102 may receive timestamps from computing system 104 as described elsewhere in this disclosure. Furthermore, in this example, hearing-assistance device 102 may write data to data log 324 indicating that the wearer has started moving with a first timestamp and data indicating that the wearer has stopped moving with a second timestamp. Computing system 104 may analyze such data to determine whether the wearer of hearing-assistance device 102 was active for the given amount of time during a time interval.

Furthermore, in some examples, as shown in FIG. 6, computing system 104 may store the body fitness measure in a database (e.g., historical data 426 (FIG. 4)) of historical body fitness measures for the wearer of hearing-assistance device 102 (610). Additionally, computing system 104 may output an indication of the historical body fitness measures (612). For example, computing system 104 may output a graph for display indicating body fitness measures over time for the wearer of hearing-assistance device 102. In some examples, the historical information may be based on an hour, day, week, month, or year, and may be presented as discrete values or a trend (e.g., graph). In some examples, to output the indication of the historical body fitness measures, computing system 104 may send to hearing-assistance device 102 audio data that represents the historical body fitness measures in audible form.

Figure 7:
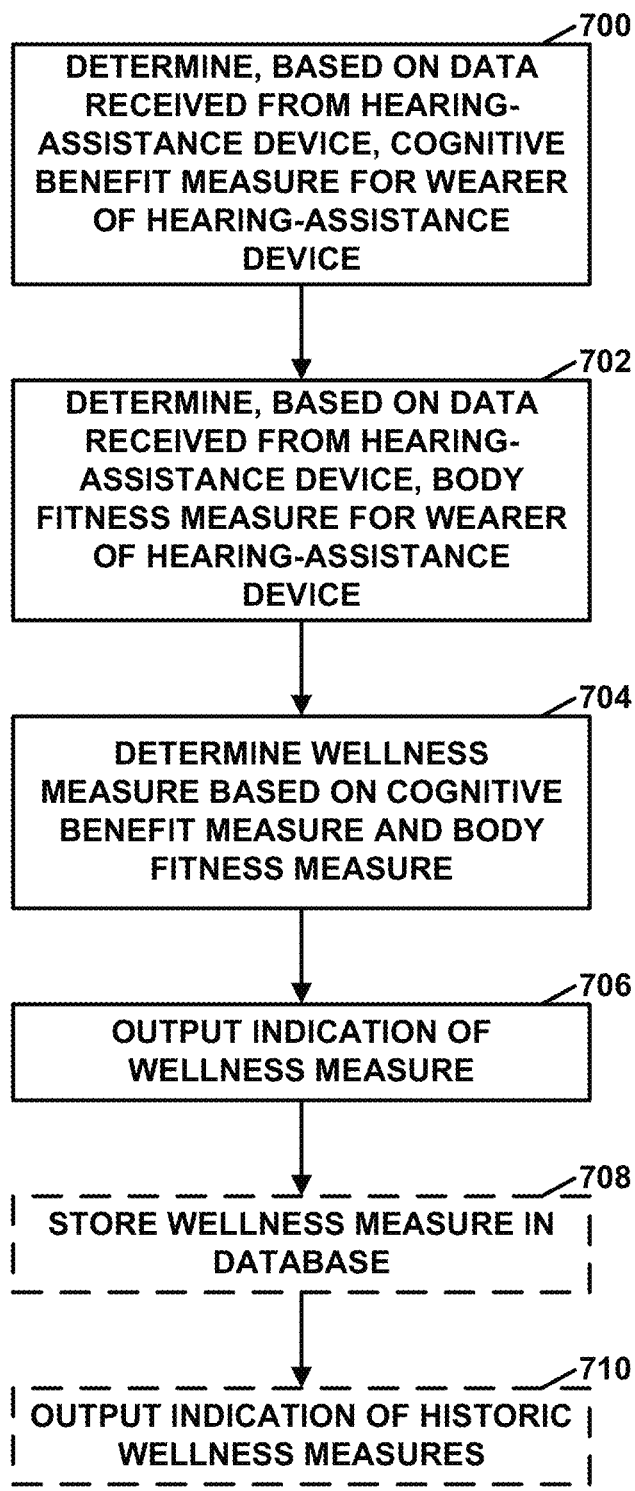
FIG. 7 is a flowchart illustrating an example operation to compute a wellness measure in accordance with one or more aspects of this disclosure.

FIG. 7 is a flowchart illustrating an example operation to compute a wellness measure in accordance with one or more aspects of this disclosure. In the example of FIG. 7, computing system 104 may determine, based on the data received from hearing-assistance device 102, a cognitive benefit measure for a wearer of hearing-assistance device 102 (700). Computing system 104 may determine the cognitive benefit measure in the manner described above with respect to FIG. 5.

Furthermore, in the example of FIG. 7, computing system 104 may determine, based on the data received from hearing-assistance device 102, a body fitness measure for the wearer of hearing-assistance device 102 (702). Computing system 104 may determine the body fitness measure in the manner described above with respect to FIG. 6.

Computing system 104 may determine a wellness measure based on the cognitive benefit measure for the wearer of hearing-assistance device 102 and the body fitness measure for the wearer of hearing-assistance device 102 (704). In various examples, computing system 104 may determine the wellness measure in various ways. For example, computing system 104 may determine the wellness measure as a weighted sum of the cognitive benefit measure and the body fitness measure. For instance, in this example, computing system 104 may determine the wellness measure with equal weightings, e.g., a 50% weighting to the cognitive benefit measure and 50% weighting to the body fitness measure. In other examples, computing system 104 may use unbalanced (i.e., different) weightings of the cognitive benefit measure and the body fitness measure. The weighting for the cognitive benefit measure may be greater than the weighting for the body fitness measure. Alternatively, the weighting for the cognitive benefit measure may be less than the weighting for the body fitness measure. As one example, computing system 104 may determine the wellness measure with a 60% weighting to the cognitive benefit measure and a 40% weighting to the body fitness measure.

Figure 10:
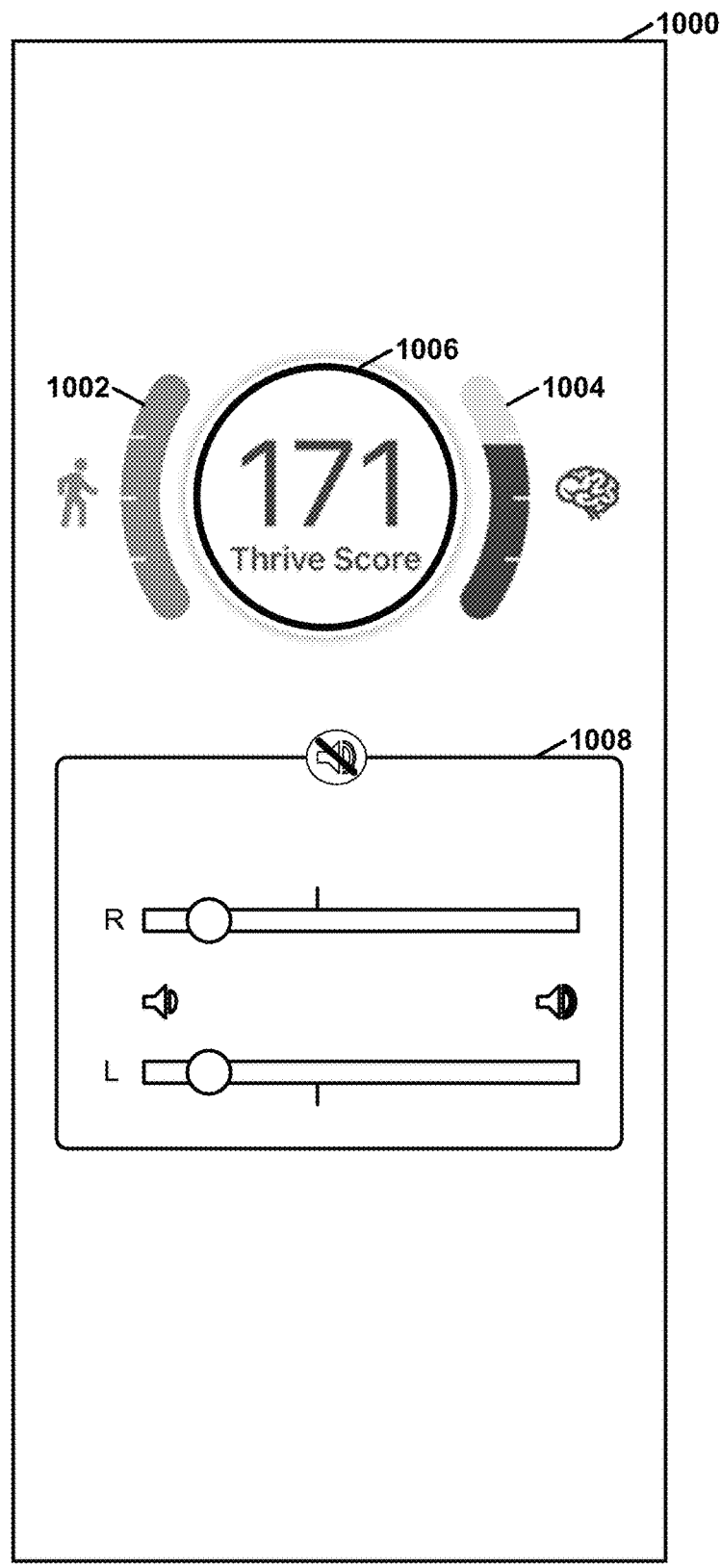
FIG. 10 is an example GUI for display of a wellness measure in accordance with one or more aspects of this disclosure.

In the example of FIG. 7, computing system 104 may output an indication of the wellness measure (706). For example, computing system 104 may output a GUI for display that includes a numerical value indicating the wellness measure. FIG. 10, described in detail below, is an example GUI for display of the wellness measure. In some examples, to output the indication of the wellness measure, computing system 104 may send to hearing-assistance device 102 audio data that represents the wellness measure in audible form.

Furthermore, in some examples, as shown in FIG. 7, computing system 104 may store the wellness measure in a database (e.g., historical data 426 (FIG. 4)) of historical wellness measures for the wearer of hearing-assistance device 102 (708). Additionally, computing system 104 may output an indication of the historical wellness measures (710). For example, computing system 104 may output a graph for display indicating wellness measures over time for the wearer of hearing-assistance device 102. In some examples, the historical information may be based on an hour, day, week, month, or year, and may be presented as discrete values or a trend (e.g., graph). In some examples, to output the indication of the historical wellness measures, computing system 104 may send to hearing-assistance device 102 audio data that represents the historical wellness measures in audible form.

Figure 8:
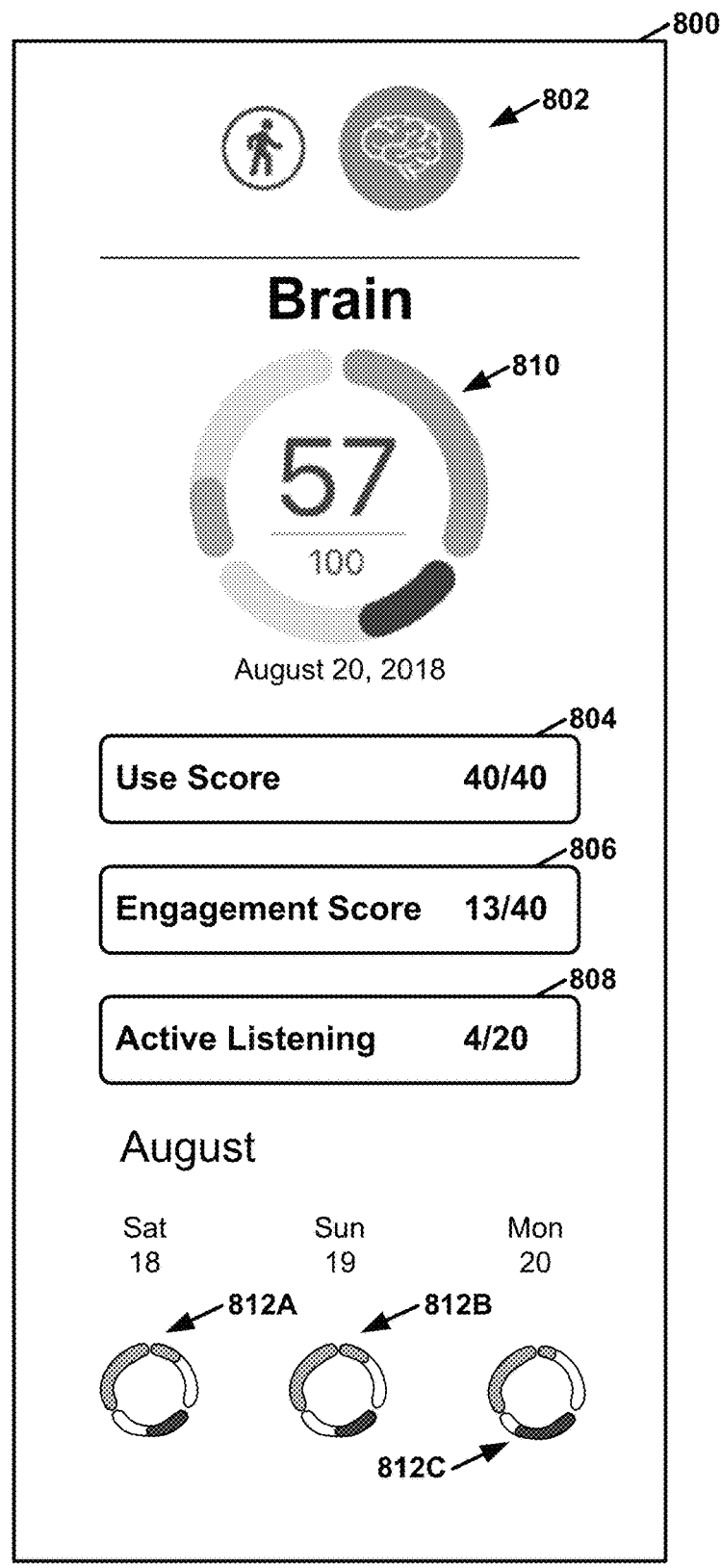
FIG. 8 is an example graphical user interface (GUI) for display of a cognitive benefit measure in accordance with one or more aspects of this disclosure.

FIG. 8 is an example GUI 800 for display of a cognitive benefit measure in accordance with one or more aspects of this disclosure. In the example of FIG. 8, GUI 800 includes controls 802 that allow a user to switch between a user interface for display of the cognitive benefit measure and a user interface for display of a body fitness measure.

In the example of FIG. 8, the cognitive benefit measure is based on a use score sub-component, an engagement score sub-component, and an active listening sub-component. Computing system 104 may determine the use score sub-component, the engagement score sub-component, and the active listening sub-component in the manner described in any of the examples provided elsewhere in this disclosure. Feature 804 of GUI 800 indicates a value of the use score sub-component. Feature 806 of GUI 800 indicates a value of the engagement score sub-component. Feature 808 of GUI 800 indicates a value of the active listening sub-component. In features 804, 806, and 808 of GUI 800, the value before the "I" mark indicates a current value of the sub-component and the value after the "I" mark indicates a goal for the sub-component.

Furthermore, in the example of FIG. 8, GUI 800 includes a circular diagram 810 having segments corresponding to the sub-components of the cognitive benefit measure. Each of the segments is filled in an amount proportional to the wearer's progress toward meeting the goals for the sub-components of the cognitive benefit measure. Additionally, circular diagram 810 may include a numerical value indicating the wearer's cognitive benefit measure (e.g., 57 in the example of FIG. 8) and a numerical value indicating the wearer's cognitive benefit measure goal for the cognitive benefit measure (e.g., 100 in the example of FIG. 8). The wearer's cognitive benefit measure goal is the wearer's goal for the cognitive benefit measure.

GUI 800 also includes historical icons 812A, 812B, and 812C (collectively, "historical icons 812"). In the example of FIG. 8, like circular diagram 810, historical icons 812 include segments with filled portions corresponding to indicate the wearer's progress toward meeting the goals for the sub-components on previous days, e.g., Saturday, Sunday and Monday in the example of FIG. 8. In response to receiving an indication of user selection of one of historical icons 812, computing system 104 may output for display a GUI having more details regarding the wearer's cognitive benefit measure for the day corresponding to the selected historical icon.

FIG. 9 is an example GUI 900 for display of a body fitness measure in accordance with one or more aspects of this disclosure. In the example of FIG. 9, GUI 900 includes controls 902 that allow a user to switch between a user interface for display of the cognitive benefit measure and a user interface for display of a body fitness measure.

In the example of FIG. 9, the body fitness measure is based on a steps sub-component, an activity sub-component, and a movement sub-component. Computing system 104 may determine the steps sub-component, the activity sub-component, and the movement sub-component in the manner described in any of the examples provided elsewhere in this disclosure. Feature 904 of GUI 900 indicates a value of the steps sub-component. Feature 906 of GUI 900 indicates a value of the activity sub-component. Feature 908 of GUI 900 indicates a value of the movement sub-component. In features 904, 906, and 908 of GUI 900, the value before the "I" mark indicates a current value of the sub-component and the value after the "I" mark indicates a goal for the sub-component.

Furthermore, in the example of FIG. 9, GUI 900 includes a circular diagram 910 having segments corresponding to the sub-components of the body fitness measure. Each of the segments is filled in an amount proportional to the wearer's progress toward meeting the goals for the sub-components of the body fitness measure. Additionally, circular diagram 910 may include a numerical value indicating the wearer's body fitness measure (e.g., 100 in the example of FIG. 9) and a numerical value indicating the wearer's body fitness measure goal (e.g., 100 in the example of FIG. 9).

GUI 900 also includes historical icons 912A, 912B, and 912C (collectively, "historical icons 912"). Like circular diagram 910, historical icons 912 include segments with filled portions corresponding to the wearer's progress toward meeting the goals for the sub-components on previous days, e.g., Saturday, Sunday and Monday in the example of FIG. 9. In response to receiving an indication of user selection of one of historical icons 912, computing system 104 may output for display a GUI having more details regarding the wearer's cognitive benefit measure for the day corresponding to the selected historical circular diagram.

FIG. 10 is an example GUI 1000 for display of a wellness measure in accordance with one or more aspects of this disclosure. In the example of FIG. 10, GUI 1000 includes a body fitness measure feature 1002 and a cognitive benefit measure feature 1004. Body fitness measure feature 1002 is filled in an amount proportional to the wearer's progress toward meeting the wearer's body fitness measure goal. Cognitive benefit measure feature 1004 is filled in an amount proportional to the wearer's progress toward meeting the wearer's cognitive benefit measure goal. The wearer's cognitive benefit measure goal may also be referred to herein as the cognitive benefit measure goal. Additionally, in the example of FIG. 10, GUI 1000 includes a wellness measure feature 1006 (e.g., indicated by "Thrive Score" in FIG. 10) that includes a numeric value indicating the wearer's wellness measure.

In the example of FIG. 10, GUI 100 may be a primary screen of companion application 424. Because controlling the volume of hearing-assistance device(s) may be the feature for which the user uses companion application 424 the most, GUI 1000 may be designed to indicate the wearer's wellness measure along with volume controls 1008 in order to bring the wearer's wellness measure to the user's attention.

In some examples, a processing system (e.g., in computing system 104, hearing-assistance device 102, or another device) may detect one or more user behavior conditions using hearing-assistance device 102. The processing system may comprise one or more processors. The user behavior conditions may be measures of behavior of the wearer of hearing-assistance device 102. In this example, the processing system may determine a wellness measure based on the one or more conditions.

The user behavior conditions may include the cognitive benefit measure, the body fitness measure, or other measures of the behavior of the wearer of hearing-assistance device 102. For instance, the cognitive benefit measure may be considered a measure of user behavior with respect to how the wearer of hearing-assistance device 102 uses hearing-assistance device 102. Similarly, the body fitness measure may be considered a measure of user behavior with respect to physical activity behavior in which the wearer of hearing-assistance device 102 engages. Thus, detecting one or more user behavior conditions may include detecting activity information (e.g., the body fitness measure) and detecting hearing information (e.g., the cognitive benefit measure). For instance, the processing system may determine a cognitive measure and a body measure. The processing system may further determine the wellness measure using the cognitive measure and the body measure. In some such examples, hearing-assistance device 102 determines the wellness measure.

In some examples, the processing system may determine the wellness measure based at least in part on the activity information and the hearing information. In some examples, the hearing information includes one or more of hearing aid usage, user engagement, and active listening. In some examples, information relating to the user behavior conditions may be wirelessly transmitted from the hearing-assistance device to a computing device (e.g., a computing device in computing system 104) and the computing device determines the wellness measure using the transmitted information.

The following paragraphs provide examples in accordance with techniques of this disclosure.

Example 1. A method comprising: receiving, by a computing system comprising one or more electronic computing devices, data from a hearing-assistance device; determining, by a computing system, based on the data received from the hearing-assistance device, a cognitive benefit measure for a wearer of the hearing-assistance device, the cognitive benefit measure being an indication of a change of a cognitive benefit of the wearer of the hearing-assistance device attributable to use of the hearing-assistance device by the wearer of the hearing-assistance device; and outputting, by the computing system, an indication of the cognitive benefit measure.

Example 2. The method of example 1, wherein determining the cognitive benefit measure comprises: determining, by the computing system, a plurality of sub-components of the cognitive benefit measure; and determining, by the computing system, the cognitive benefit measure based on the plurality of sub-components of the cognitive benefit measure.

Example 3. The method of example 2, wherein determining the plurality of sub-components comprises one or more of: determining, by the computing system, an audibility sub-component is a measure of an improvement in audibility provided to the wearer by the hearing-assistance device, determining, by the computing system, an intelligibility sub-component that indicates a measure of an improvement in speech understanding provided by the hearing-assistance device, determining, by the computing system, a comfort sub-component that indicates a measure of noise reduction provided by the hearing-assistance device, determining, by the computing system, a focus sub-component that indicates a measure of time the hearing-assistance device spends in directional processing modes, each of the respective directional processing modes selectively attenuating off-axis, unwanted sounds, determining, by the computing system, a sociability sub-component that indicates a measure of time spent in auditory environments involving speech, or determining, by the computing system, a connectivity sub-component that indicates a measure of an amount of time the hearing-assistance device spent streaming media from devices connected wirelessly to the hearing-assistance device.

Example 4. The method of any of examples 2 or 3, wherein determining the cognitive benefit measure comprises determining, by the computing system, a weighted average of the plurality of sub-components.

Example 5. The method of any of examples 2 or 4, wherein determining the plurality of sub-components comprises one or more of: determining, by the computing system, a use score sub-component that is based on how much time the wearer of the hearing-assistance device uses the hearing-assistance device during a scoring period, determining, by the computing system, an engagement score sub-component that is a measure of how much the wearer of the hearing-assistance device participates in activities involving aural engagement during the scoring period, or determining, by the computing system, an active listening sub-component based on exposure of the wearer of the hearing-assistance device to a plurality of different acoustic environments during the scoring period.

Example 6. The method of any of examples 1-5, further comprising: receiving, by the computing system, an indication of user input to access a cognitive benefit section of a graphical user interface (GUI) of a software application running on the computing system; and in response to receiving the indication of user input, sending, by the computing system, a request to the hearing-assistance device, wherein the computing system receives the data from the hearing-assistance device in response to the request.

Example 7. The method of example 6, wherein determining the cognitive benefit measure comprises scaling, by the computing system, the cognitive benefit measure based on an amount of time the wearer spends wearing the hearing-assistance device.

Example 8. The method of any of examples 1-7, further comprising: storing, by the computing system, the cognitive benefit measure in a database of historical cognitive benefit measures for the wearer; and outputting, by the computing system, an indication of the historical cognitive benefit measures.

Example 9. The method of any of examples 1-8, further comprising: determining, by the computing system, based on the data received from the hearing-assistance device, a body measure for the wearer of the hearing-assistance device, the body measure being an indication of physical activity in which the wearer of the hearing-assistance device engages while wearing the hearing-assistance device; and outputting, by the computing system, an indication of the body measure.

Example 10. The method of example 9, further comprising: determining, by the computing system, based on the cognitive benefit measure and the body measure, a wellness measure for the wearer of the hearing-assistance device, the wellness measure for the wearer of the hearing-assistance device being an indication of an overall wellness of the wearer of the hearing-assistance device; and outputting, by the computing system, an indication of the wellness measure.

Example 11. The method of any of examples 1-10, wherein: the method further comprises sending, by the computing system, timestamps to the hearing-assistance device, receiving the data from the hearing-assistance device comprises receiving, by the computing system, a plurality of log data items, each of the log data items comprising log data and one of the timestamps, and determining the cognitive benefit measure comprises determining, by the computing system, the cognitive benefit measure based on the timestamps and the log data in the log data items.

Example 12. The method of any of examples 1-11, further comprising: sending, by the computing system, based on the cognitive benefit measure, an alert to the wearer of the hearing-assistance device or another person.

Example 13. A computing system comprising: a radio configured to receive data from a hearing-assistance device; and one or more processors configured to: determine, based on the data received from the hearing-assistance device, a cognitive benefit measure for a wearer of the hearing-assistance device, the cognitive benefit measure being an indication of a change of a cognitive benefit of the wearer of the hearing-assistance device attributable to use of the hearing-assistance device by the wearer of the hearing-assistance device; and output an indication of the cognitive benefit measure.

Example 14. The computing system of example 13, wherein the one or more processors are configured to: determine a plurality of sub-components of the cognitive benefit measure; and determine the cognitive benefit measure based on the plurality of sub-components of the cognitive benefit measure.

Example 15. The computing system of example 14, wherein the one or more processors are configured such that, as part of determining the plurality of sub-components, the one or more processors determine one or more of: an audibility sub-component that is a measure of an improvement in audibility provided to the wearer by the hearing-assistance device, an intelligibility sub-component that indicates a measure of an improvement in speech understanding provided by the hearing-assistance device, a comfort sub-component that indicates a measure of noise reduction provided by the hearing-assistance device, a focus sub-component that indicates a measure of time the hearing-assistance device spends in directional processing modes, each of the respective directional processing modes selectively attenuating off-axis, unwanted sounds, a sociability sub-component that indicates a measure of time spent in auditory environments involving speech, or a connectivity sub-component that indicates a measure of an amount of time the hearing-assistance device spent streaming media from devices connected wirelessly to the hearing-assistance device.

Example 16. The computing system of any of examples 14 or 15, wherein the one or more processors are configured such that, as part of determining the cognitive benefit measure, the one or more processors determine a weighted average of the plurality of sub-components.

Example 17. The computing system of any of examples 14 or 16, wherein the one or more processors are configured such that, as part of determining the plurality of sub-components, the one or more processors determine one or more of: a use score sub-component that is based on how much time the wearer of the hearing-assistance device uses the hearing-assistance device during a scoring period, an engagement score sub-component that is a measure of how much the wearer of hearing-assistance device participates in activities involving aural engagement during the scoring period, or an active listening sub-component based on exposure of the wearer of the hearing-assistance device to a plurality of different acoustic environments during the scoring period.

Example 18. The computing system of any of examples 13-17, wherein the one or more processors are further configured to: receive an indication of user input to access a cognitive benefit section of a graphical user interface (GUI) of a software application running on the computing system; and in response to receiving the indication of user input, send a request to the hearing-assistance device, wherein the computing system receives the data from the hearing-assistance device in response to the request.

Example 19. The computing system of any of examples 13-18, wherein the one or more processors are configured such that, as part of determining the cognitive benefit measure, the one or more processors scale the cognitive benefit measure based on an amount of time the wearer spends wearing the hearing-assistance device.

Example 20. The computing system of any of examples 13-19, wherein the one or more processors are further configured to: store the cognitive benefit measure in a database of historical cognitive benefit measures for the wearer; and output an indication of the historical cognitive benefit measures.

Example 21. The computing system of any of examples 13-20, wherein the one or more processors are further configured to: determine, based on the data received from the hearing-assistance device, a body measure for the wearer of the hearing-assistance device, the body measure being an indication of physical activity in which the wearer of the hearing-assistance device engages while wearing the hearing-assistance device; and output an indication of the body measure.

Example 22. The computing system of example 21, wherein the one or more processors are further configured to: determine, based on the cognitive benefit measure and the body measure, a wellness measure for the wearer of the hearing-assistance device, the wellness measure for the wearer of the hearing-assistance device being an indication of an overall wellness of the wearer of the hearing-assistance device; and output an indication of the wellness measure.

Example 23. The computing system of any of examples 13-22, wherein: the one or more processors are configured to cause the computing system to send timestamps to the hearing-assistance device, the computing system is configured to receive a plurality of log data items from the hearing-assistance device, each of the log data items comprising log data and one of the timestamps, and the one or more processors are configured to determine the cognitive benefit measure based on the timestamps and the log data in the log data items.

Example 24. The computing system of any of examples 13-24, wherein the one or more processors are further configured to: send, based on the cognitive benefit measure, an alert to the wearer of the hearing-assistance device or another person.

Example 25. A non-transitory computer-readable storage medium having instructions stored thereon that, when executed, cause a computing system to: receive data from a hearing-assistance device; determine, based on the data received from the hearing-assistance device, a cognitive benefit measure for a wearer of the hearing-assistance device, the cognitive benefit measure being an indication of a change of a cognitive benefit of the wearer of the hearing-assistance device attributable to use of the hearing-assistance device by the wearer of the hearing-assistance device; and output an indication of the cognitive benefit measure.

Example 26. The non-transitory computer-readable storage medium having instructions stored thereon that, when executed, cause the one or more processors to perform the methods of any of examples 13-24.

Example 27. A computing system comprising: means for receiving data from a hearing-assistance device; and means for determining, based on the data received from the hearing-assistance device, a cognitive benefit measure for a wearer of the hearing-assistance device, the cognitive benefit measure being an indication of a change of a cognitive benefit of the wearer of the hearing-assistance device attributable to use of the hearing-assistance device by the wearer of the hearing-assistance device; and means for outputting an indication of the cognitive benefit measure.

Example 28. The computing system of example 27, the means for determining the cognitive benefit measure comprises: means for determining a plurality of sub-components of the cognitive benefit measure; and means for determining the cognitive benefit measure based on the plurality of sub-components of the cognitive benefit measure.

Example 29. The computing system of example 28, the means for determining the plurality of sub-components comprises means for determining one or more of: an audibility sub-component that is a measure of an improvement in audibility provided to the wearer by the hearing-assistance device, an intelligibility sub-component that indicates a measure of an improvement in speech understanding provided by the hearing-assistance device, a comfort sub-component that indicates a measure of noise reduction provided by the hearing-assistance device, a focus sub-component that indicates a measure of time the hearing-assistance device spends in directional processing modes, each of the respective directional processing modes selectively attenuating off-axis, unwanted sounds, a sociability sub-component that indicates a measure of time spent in auditory environments involving speech, or a connectivity sub-component that indicates a measure of an amount of time the hearing-assistance device spent streaming media from devices connected wirelessly to the hearing-assistance device.

Example 30. The computing system of any of examples 28 or 29, wherein the means for determining the cognitive benefit measure comprises means for determining a weighted average of the plurality of sub-components.

Example 31. The computing system of any of examples 28 or 30, wherein the means for determining the plurality of sub-components comprises means for determining one or more of:
a use score sub-component that is based on how much time the wearer of the hearing-assistance device uses the hearing-assistance device during a scoring period, an engagement score sub-component that is a measure of how much the wearer of hearing-assistance device participates in activities involving aural engagement during the scoring period, or an active listening sub-component based on exposure of the wearer of the hearing-assistance device to a plurality of different acoustic environments during the scoring period.

Example 31. The computing system of any of examples 27-30, further comprising: means for receiving an indication of user input to access a cognitive benefit section of a graphical user interface (GUI) of a software application running on the computing system; and means for sending, in response to receiving the indication of user input, a request to the hearing-assistance device, wherein the computing system receives the data from the hearing-assistance device in response to the request.

Example 32. The computing system of any of examples 27-31, wherein the means for determining the cognitive benefit measure comprises means for scaling the cognitive benefit measure based on an amount of time the wearer spends wearing the hearing-assistance device.

Example 33. The computing system of any of examples 27-32, further comprising: means for storing the cognitive benefit measure in a database of historical cognitive benefit measures for the wearer; and means for outputting an indication of the historical cognitive benefit measures.

Example 34. The computing system of any of examples 27-33, further comprising: means for determining, based on the data received from the hearing-assistance device, a body measure for the wearer of the hearing-assistance device, the body measure being an indication of physical activity in which the wearer of the hearing-assistance device engages while wearing the hearing-assistance device; and means for outputting an indication of the body measure.

Example 35. The computing system of example 34, further comprising: means for determining, based on the cognitive benefit measure and the body measure, a wellness measure for the wearer of the hearing-assistance device, the wellness measure for the wearer of the hearing-assistance device being an indication of an overall wellness of the wearer of the hearing-assistance device; and means for outputting an indication of the wellness measure.

Example 36. The computing system of any of examples 27-35, further comprising: means for causing the computing system to send timestamps to the hearing-assistance device; means for receiving a plurality of log data items from the hearing-assistance device, each of the log data items comprising log data and one of the timestamps, and means for determining the cognitive benefit measure based on the timestamps and the log data in the log data items.

Example 37. The computing system of any of examples 27-36, further comprising means for sending, based on the cognitive benefit measure, an alert to the wearer of the hearing-assistance device or another person.

Example 38. A method comprising: detecting one or more user behavior conditions using a hearing-assistance device; and determining a wellness measure based on the one or more conditions.

Example 39. The method of example 38, wherein detecting one or more user behavior conditions includes detecting activity information and detecting hearing information, and the wellness measure is based at least in part on the activity information and the hearing information.

Example 40. The method of example 39, wherein the hearing information includes one or more of hearing aid usage, user engagement, and active listening.

Example 41. The method of examples 38 or 39, further comprising wirelessly transmitting information relating to the user behavior conditions from the hearing-assistance device to a computing device, and the computing device determines the wellness measure using the transmitted information.

Example 42. The method of any one or any combination of examples 38-41, comprising determining a cognitive measure and a body measure, and determining the wellness measure using the cognitive measure and the body measure.

Example 43. The method of any one or any combination of examples 38-42, wherein the hearing-assistance device determines the wellness measure.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A method comprising:
    receiving, by a computing system comprising one or more electronic computing devices, data from a hearing-assistance device;
    determining, by the computing system, based on the data received from the hearing-assistance device, an amount of time that a wearer of the hearing-assistance device spends in conversation;
    determining, by the computing system, based on the amount of time that the wearer of the hearing-assistance device spends in conversation, a wellness measure for the wearer of the hearing-assistance device; and
    outputting, by the computing system, an indication of the wellness measure.

2. The method of claim 1, wherein:
    the method further comprises determining, by the computing system, based on the data received from the hearing-assistance device, a body measure for the wearer of the hearing-assistance device, the body measure being an indication of physical activity in which the wearer of the hearing-assistance device engaged while wearing the hearing-assistance device; and
    determining the wellness measure comprises determining, by the computing system, the wellness measure based on the body measure and the amount of time that the wearer of the hearing-assistance device spends in conversation.

3. The method of claim 1, wherein:
    the method further comprises determining, by the computing system, a plurality of sub-components, the plurality of sub-components including the amount of time that the wearer of the hearing-assistance device spends in conversation and one or more of:
        an audibility sub-component that indicates a measure of an improvement in audibility provided to the wearer by the hearing-assistance device,
        an intelligibility sub-component that indicates a measure of an improvement in speech understanding provided by the hearing-assistance device,
        a comfort sub-component that indicates a measure of noise reduction provided by the hearing-assistance device,
        a focus sub-component that indicates a measure of time the hearing-assistance device spends in directional processing modes, each of the respective directional processing modes selectively attenuating off-axis, unwanted sounds, or
        a connectivity sub-component that indicates a measure of an amount of time the hearing-assistance device spent streaming media from devices connected wirelessly to the hearing-assistance device, and
    determining the wellness measure comprises determining, by the computing system, the wellness measure based on one or more of the plurality of sub-components.

4. The method of claim 3, further comprising outputting, by the computing system, a user interface that indicates values for the plurality of sub-components.

5. The method of claim 3, wherein:
the method further comprises determining a cognitive benefit measure based on the plurality of sub-components, wherein the cognitive benefit measure is an indication of a cognitive benefit of the wearer of the hearing-assistance device attributable to use of the hearing-assistance device by the wearer of the hearing-assistance device,
determining the wellness measure comprises determining, by the computing system, the wellness measure based on the cognitive benefit measure.

6. The method of claim 1, further comprising:
receiving, by the computing system, an indication of user input to access a cognitive benefit section of a graphical user interface (GUI) of a software application running on the computing system; and
in response to receiving the indication of user input, sending, by the computing system, a request to the hearing-assistance device,
wherein the computing system receives the data from the hearing-assistance device in response to the request.

7. The method of claim 1, wherein the wellness measure for the wearer of the hearing-assistance device is an indication of an overall wellness of the wearer of the hearing-assistance device.

8. A computing system comprising:
a communication unit configured to receive data from a hearing-assistance device; and
one or more processors implemented in circuitry, the one or more processors configured to:
determine, based on the data received from the hearing-assistance device, an amount of time that a wearer of the hearing-assistance device spends in conversation;
determine, based on the amount of time that the wearer of the hearing-assistance device spends in conversation, a wellness measure for the wearer of the hearing-assistance device; and
output an indication of the wellness measure.

9. The computing system of claim 8, wherein:
the one or more processors are further configured to determine, based on the data received from the hearing-assistance device, a body measure for the wearer of the hearing-assistance device, the body measure being an indication of physical activity in which the wearer of the hearing-assistance device engaged while wearing the hearing-assistance device; and
the one or more processors are configured to determine the wellness measure based on the body measure and the amount of time that the wearer of the hearing-assistance device spends in conversation.

10. The computing system of claim 8, wherein the one or more processors are configured to determine a plurality of sub-components, the plurality of sub-components including the amount of time that the wearer of the hearing-assistance device spends in conversation and one or more of:
an audibility sub-component that indicates a measure of an improvement in audibility provided to the wearer by the hearing-assistance device,
an intelligibility sub-component that indicates a measure of an improvement in speech understanding provided by the hearing-assistance device,
a comfort sub-component that indicates a measure of noise reduction provided by the hearing-assistance device,
a focus sub-component that indicates a measure of time the hearing-assistance device spends in directional processing modes, each of the respective directional processing modes selectively attenuating off-axis, unwanted sounds, or
a connectivity sub-component that indicates a measure of an amount of time the hearing-assistance device spent streaming media from devices connected wirelessly to the hearing-assistance device, and
the one or more processors are configured to determine the wellness measure based on one or more of the plurality of sub-components.

11. The computing system of claim 10, wherein the one or more processors are further configured to output a user interface that indicates values for the plurality of sub-components.

12. The computing system of claim 10,
the one or more processors are configured to determine a cognitive benefit measure based on the plurality of sub-components, wherein the cognitive benefit measure is an indication of a cognitive benefit of the wearer of the hearing-assistance device attributable to use of the hearing-assistance device by the wearer of the hearing-assistance device, and
the one or more processors are configured to determine the wellness measure based on the cognitive benefit measure.

13. The computing system of claim 8, wherein the one or more processors are further configured to:
receive an indication of user input to access a cognitive benefit section of a graphical user interface (GUI) of a software application running on the computing system; and
in response to receiving the indication of user input, send a request to the hearing-assistance device,
wherein the computing system receives the data from the hearing-assistance device in response to the request.

14. The computing system of claim 8, wherein the wellness measure for the wearer of the hearing-assistance device is an indication of an overall wellness of the wearer of the hearing-assistance device.

15. A non-transitory computer-readable storage medium having instructions stored thereon that, when executed, cause a computing system to:
receive data from a hearing-assistance device;
determine, based on the data received from the hearing-assistance device, an amount of time that a wearer of the hearing-assistance device spends in conversation;
determine, based on the amount of time that the wearer of the hearing-assistance device spends in conversation, a wellness measure for the wearer of the hearing-assistance device; and
output an indication of the wellness measure.

16. The non-transitory computer-readable storage medium of claim 15, wherein:
execution of the instructions further causes the computing system to determine, based on the data received from the hearing-assistance device, a body measure for the wearer of the hearing-assistance device, the body measure being an indication of physical activity in which the wearer of the hearing-assistance device engaged while wearing the hearing-assistance device; and
execution of the instructions causes the computing system to determine the wellness measure based on the body measure and the amount of time that the wearer of the hearing-assistance device spends in conversation.

\* \* \* \* \*